(12) United States Patent
Robberecht

(10) Patent No.: US 9,187,784 B2
(45) Date of Patent: Nov. 17, 2015

(54) EPHA4 IS A DISEASE MODIFIER IN MOTOR NEURON DISEASE

(75) Inventor: Wim Robberecht, Kumtich (BE)

(73) Assignees: VIB VZW, Gent (BE); Life Sciences Research Partners VZW, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 14/117,591

(22) PCT Filed: May 14, 2012

(86) PCT No.: PCT/EP2012/058877
§ 371 (c)(1),
(2), (4) Date: Feb. 3, 2014

(87) PCT Pub. No.: WO2012/156351
PCT Pub. Date: Nov. 22, 2012

(65) Prior Publication Data
US 2014/0143897 A1 May 22, 2014

(30) Foreign Application Priority Data
May 13, 2011 (GB) .................................. 1107996.9

(51) Int. Cl.
*A61K 31/40* (2006.01)
*C12Q 1/68* (2006.01)
*A61K 38/17* (2006.01)
*A61K 49/00* (2006.01)

(52) U.S. Cl.
CPC .............. *C12Q 1/6876* (2013.01); *A61K 31/40* (2013.01); *A61K 38/1793* (2013.01); *A61K 49/0008* (2013.01)

(58) Field of Classification Search
CPC  A61K 31/40; A61K 38/1793; A61K 49/0008
See application file for complete search history.

(56) References Cited

U.S. PATENT DOCUMENTS

| | | |
|---|---|---|
| 2009/0069315 A1 | 3/2009 | Sivasankaran et al. |
| 2010/0113415 A1 | 5/2010 | Rajapakse et al. |
| 2010/0197688 A1 | 8/2010 | Nantermet et al. |

FOREIGN PATENT DOCUMENTS

| | | |
|---|---|---|
| EP | 2260864 A1 | 12/2010 |
| JP | 2010285413 A | 12/2010 |
| WO | 2004028551 A9 | 4/2004 |
| WO | 2007071789 A1 | 6/2007 |
| WO | 2007103432 A9 | 9/2007 |
| WO | 2010141974 A1 | 12/2010 |
| WO | 2012156351 A1 | 11/2012 |

OTHER PUBLICATIONS

Schoonaert et al., Inhibition of the EphA4 receptor rescues the axonopathy in a zebrafish model for ALS, Society for Neuroscience Abstract Viewer and Itinerary Planner, 2011, vol. 41.

Murai et al., Targeting the EphA4 receptor in the nervous system with biologically active peptides, Molecular and Cellular Neuroscience, Dec. 2003, pp. 1000-1011, vol. 24, No. 4.

Noberini et al., Small molecules can selectively inhibit ephrin binding to the EphA4 and EphA2 receptors, Journal of Biological Chemistry, Oct. 24, 2008, pp. 29461-29472, vol. 283, No. 43.

PCT International Search Report, PCT/EP2012/058877 dated Aug. 10, 2012.

Beattie et al., Fishing for a Mechanism: Using Zebrafish to Understand Spinal Muscular Atrophy, Journal of Child Neurology, Aug. 2007, pp. 995-1003, vol. 22, No. 8.

*Primary Examiner* — John Ulm
(74) *Attorney, Agent, or Firm* — TraskBritt, P.C.

(57) ABSTRACT

The present application relates to the field of motor neuron diseases, most particularly to amyotrophic lateral sclerosis and spinomuscular atrophy. Provided herein are strategies to improve symptoms and increase survival in patients with these axonopathies by inhibiting signaling mediated by the EphA4 ephrin receptor.

8 Claims, 15 Drawing Sheets

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: EphA4 inhibitory peptide

<400> SEQUENCE: 1

Lys Tyr Leu Pro Tyr Trp Pro Val Leu Ser Ser Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: EphA4 inhibitory peptide

<400> SEQUENCE: 2

Ala Pro Tyr Cys Val Tyr Arg Gly Ser Trp Ser Cys
1               5                   10

<210> SEQ ID NO 3
<211> LENGTH: 12
<212> TYPE: PRT
```

<213> ORGANISM: Artificial Sequence
<220> FEATURE:
<223> OTHER INFORMATION: EphA4 inhibitory peptide

<400> SEQUENCE: 3

Val Thr Met Glu Ala Ile Asn Leu Ala Phe Pro Gly
1               5                   10

<210> SEQ ID NO 4
<211> LENGTH: 25
<212> TYPE: DNA
<213> ORGANISM: Artificial Sequence
<220> FEATURE:
<223> OTHER INFORMATION: Morpholino

<400> SEQUENCE: 4
cctcttacct cagttacaat ttata                                    25

<210> SEQ ID NO 5
<211> LENGTH: 25
<212> TYPE: DNA
<213> ORGANISM: Artificial Sequence
<220> FEATURE:
<223> OTHER INFORMATION: Morpholino

<400> SEQUENCE: 5
ctgtgaacac aagcgcagcc attgg                                    25

<210> SEQ ID NO 6
<211> LENGTH: 25
<212> TYPE: DNA
<213> ORGANISM: Artificial Sequence
<220> FEATURE:
<223> OTHER INFORMATION: Morpholino

<400> SEQUENCE: 6
aatccaaagg gtagccattt tcagg                                    25

<210> SEQ ID NO 7
<211> LENGTH: 25
<212> TYPE: DNA
<213> ORGANISM: Artificial Sequence
<220> FEATURE:
<223> OTHER INFORMATION: Morpholino

<400> SEQUENCE: 7
cctcccactg aaaatggaca gagga                                    25

<210> SEQ ID NO 8
<211> LENGTH: 22
<212> TYPE: DNA
<213> ORGANISM: Artificial Sequence
<220> FEATURE:
<223> OTHER INFORMATION: Morpholino

<400> SEQUENCE: 8
cgacatcttc tgcaccattg gc                                       22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9

```
cggaattacc cagagaatga ag                                              22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
aaactgtgtg gaggacattt gg                                              22
```

EPHA4 IS A DISEASE MODIFIER IN MOTOR NEURON DISEASE

CROSS-REFERENCE TO RELATED APPLICATIONS

This application is a national phase entry under 35 U.S.C. §371 of International Patent Application PCT/EP2012/058877, filed May 14, 2012, designating the United States of America and published in English as International Patent Publication WO 2012/156351 A1 on Nov. 22, 2012, which claims the benefit under Article 8 of the Patent Cooperation Treaty and under 35 U.S.C. §119(e) to Great Britain Patent Application Serial No. 1107996.9, filed May 13, 2011.

TECHNICAL FIELD

The present application relates generally to biotechnology and medicine, and more particularly to the field of motor neuron diseases, most particularly to amyotrophic lateral sclerosis and spinomuscular atrophy. Provided herein are strategies to improve symptoms and increase survival in patients with these axonopathies by inhibiting signaling mediated by the EphA4 ephrin receptor.

BACKGROUND

Amyotrophic lateral sclerosis (ALS) is a relentlessly progressive, fatal degenerative disorder mainly, but not exclusively, affecting motor neurons. The disease is characterized by progressive muscle weakness, atrophy and spasticity. Currently, no cure for ALS is available. Most patients suffer from the sporadic form of this disease, while approximately 10% have familial ALS. Mutations in several genes are known to cause this hereditary form. Mutations in superoxide dismutase 1 (SOD1), TAR-DNA binding protein (TARDBP) and fused in sarcoma/translated in liposarcoma (FUS/TLS), and hexanucleotide repeat expansions in C9orf72 are the most prevalent.[1-5]

Due to the word "sclerosis" (literally: "hardening") in the name, it is sometimes confused with multiple sclerosis, although they are very distinct neurological diseases. Multiple sclerosis (MS) is an inflammatory disease of white matter, primarily damaging myelin sheets of neurons. MS affects more women than men, may lead to changes in sensation (hypoesthesia), visual problems and cognitive impairment, and life expectancy for most patients exceeds 20 years.

ALS on the other hand is a grey matter disease caused by the degeneration of neurons located in the anterior horn of the spinal cord and the cortical neurons that provide their afferent input. Sensory function generally is spared, as is cognitive function and oculomotor activity. Most people with ALS die from respiratory failure, usually within three to five years from the onset of symptoms.

Although survival of ALS patients is only three to five years on average, variability of disease duration is quite large, ranging from only a few months to several decades. Even survival of patients with the same mutation in the same gene in the same family is very variable.[6,7] Similarly, age of onset can range from second to ninth decade of life.[8] Genetic factors are expected to explain this variability by modifying the phenotype, both in sporadic and familial ALS. The identification of these modifying pathways is of interest, as they are likely to reveal novel targets for intervention. Small animal models, such as flies, worms and zebrafish, are very useful for genetic and compound screening.[9-12] To this end, zebrafish models for ALS were previously developed. Overexpressing mutant SOD1 or TDP-43 in zebrafish embryos induces a motor axonopathy, characterized by shorter and aberrantly branched motor axons.[13,14] The identification of the factors underlying variability is of interest, as they may represent targets for therapeutic intervention.

DISCLOSURE

To identify factors affecting the variability of disease duration, a morpholino-based genetic screen was set up in a zebrafish model of ALS. Genetic and pharmacological inhibition of the ephrin receptor, EphA4, modified the phenotype in fish, mouse and rat models for mutant SOD1 motor neuron degeneration. The effect of EphA4 on motor neuron disease appeared generic as it also affected the phenotype induced by mutant TDP-43, another cause of ALS, and by the absence of survival motor neuron (SMN), which causes spinomuscular atrophy (SMA), a severe, early onset disorder of lower motor neurons.[15] Furthermore, the expression of EPHA4 determined disease onset and survival in patients with sporadic ALS. This indicates that the ephrin system may generically contribute to the pathogenesis of motor axonopathies, and is a novel target for therapeutic intervention in motor neuron and axon degeneration.

Accordingly, in a first aspect, inhibitors of EphA4 signaling for use in treatment of a motor neuron disease are provided.

Alternatively, this can be phrased as methods are provided for treating a motor neuron disease to a subject in need thereof, comprising administering an inhibitor of EphA4 signaling to the subject. Typically, one or more symptoms or parameters will be evaluated to check the progression of the motor neuron disease in the subject.

According to particular embodiments, the inhibitors of EphA4 signaling are inhibitors of EphA4. According to alternative embodiments, the inhibitors are inhibitors of one or more of the ligands of EphA4, or of the interaction between EphA4 and at least one of its ligands. It is particularly envisaged that the ligand to be inhibited is ephrin-B2.

The motor neuron diseases that can be treated, or whose symptoms can be improved, are typically diseases of grey matter that directly affect motor neurons. According to particular embodiments, the motor neuron diseases envisaged are G12 diseases in the ICD-10 classification of the WHO. According to alternative embodiments, the motor neuron diseases are anterior horn diseases. Most particularly, envisaged diseases for treatment are amyotrophic lateral sclerosis (ALS) and spinal muscular atrophy (SMA). ALS can be sporadic ALS or familial ALS.

According to particular embodiments, the inhibitors of EphA4 signaling are selected from 2,5-dimethylpyrrolyl benzoic acid derivatives and EphA4 inhibitory peptides, such as the KYL peptide. Most particularly, the EphA4 inhibitory peptide is selected from KYLPYWPVLSSL (SEQ ID NO:1), APYCVYRGSWSC (SEQ ID NO:2) and VTMEAINLAFPG (SEQ ID NO:3). Particularly envisaged 2,5-dimethylpyrrolyl benzoic acid derivatives include compound 1 and compound 2 (see figure, and see compound 1 and 2 in reference 22 (Noberini et al.)).

In a further aspect, EphA4 can be used as a (prognostic) biomarker for motor neuron disease. Particularly, it was found that EphA4 levels (or activity, particularly tyrosine autophosphorylation activity) inversely correlate with disease onset and with disease duration (or survival in case of lethal disease). Here also, the biomarkers for motor neuron diseases are typically for diseases of grey matter that directly affect motor neurons. According to particular embodiments, the motor neuron diseases envisaged are G12 diseases in the ICD-10 classification of the WHO. According to alternative embodiments, the motor neuron diseases are anterior horn diseases. Most particularly, envisaged diseases for treatment are amyotrophic lateral sclerosis (ALS) and spinal muscular atrophy (SMA). ALS can be sporadic ALS or familial ALS.

Accordingly, methods are provided to determine onset or progression of a motor neuron disease in a subject, comprising determining EphA4 levels and/or EphA4 activity in a sample of the subject. According to further specific embodiments, decreased EphA4 levels and/or activity are indicative of delayed onset (in a subject at risk of developing a motor neuron disease) and/or increased survival (or disease duration).

According to particular embodiments, EphA4 levels and/or activity are measured using quantitative PCR. Alternatively, EphA4 levels and/or activity may be measured by assessing presence of a mutation in the EphA4 protein. Particularly envisaged mutations include the R514X mutation (which truncates the protein, leading to decreased levels or absence of EphA4) or the R571Q mutation (which interferes with autophosphorylation activity, yielding an inactive EphA4 protein).

The biomarker can be used as a prognosis to predict disease onset, or can be used to make predictions about disease progression. Also, the biomarker can be used to monitor response to therapy. In the latter case, decrease of EphA4 levels and/or activity indicates that the patient will have increased disease duration or survival. For instance, when EphA4 inhibition is used as therapy, monitoring EphA4 levels will yield an indication of the success of the therapy.

According to a further aspect, methods of screening compounds for inhibitory activity on EphA4 signaling are provided, these methods comprising:

administering a compound of interest to an animal that has a motor neuron disease; and evaluating the inhibitory effect on EphA4 signaling by evaluating at least one parameter of the phenotype of the motor neuron disease in the animal.

Particularly envisaged animals in these animal models are zebrafish. Particularly envisaged motor neuron diseases are ALS and SMA; zebrafish models for these diseases are described in references 13 to 15.

BRIEF DESCRIPTION OF THE FIGURES

FIG. 8, Panel D is a graph depicting percentage EphA4 expression versus time in SOD1 mice.

DETAILED DESCRIPTION

Definitions

Figure 1:
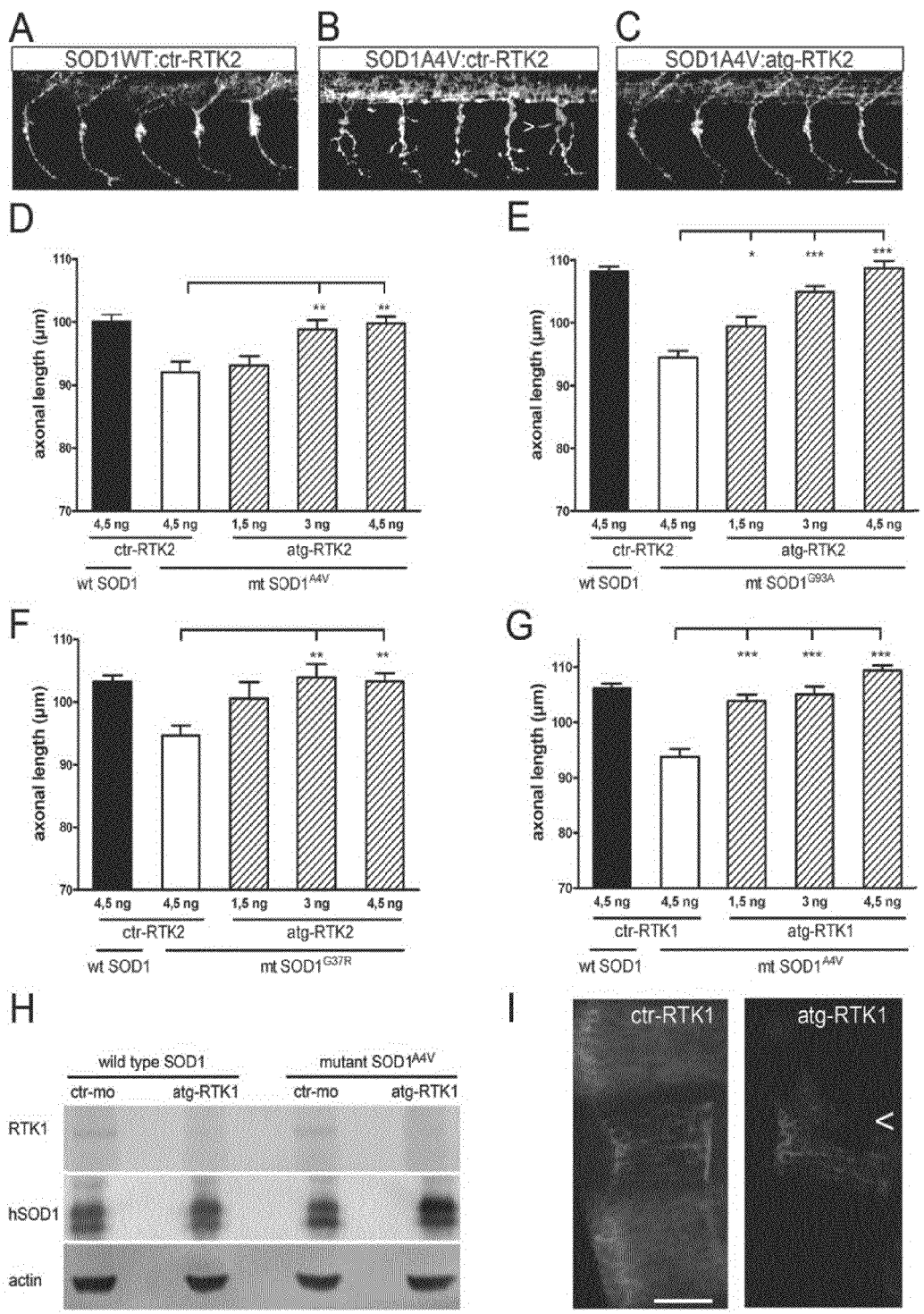
FIG. 1: EphA4 knockdown rescues mutant SOD1-induced motor axonopathy. Immunostaining for synaptic vesicle 2 (SV2) shows the motor axon in 30 hpf (hours post-fertilization) old zebrafish embryos expressing SOD1 WT, injected with non-functional five-base pair-mismatch control morpholino (ctr-RTK2) (Panel A), SOD1A4V, injected with ctr-RTK2 (Panel B), and SOD1A4V, injected with atg-RTK2 (Panel C). Abnormal branching is indicated with arrowhead. Y-axes show motor axon length of zebrafish embryos expressing wild-type SOD1 (black bar, Panels D-G) or mutant SOD1 (white bar, Panels D-G). Knockdown of RTK2 in SOD1A4V- (Panel D), SOD1G93A- (Panel E) and SOD1G37R- (Panel F) expressing fish was established by co-injection of increasing amounts of atg-RTK2 morpholino (shaded bars). RTK1 expression was inhibited in SOD1A4V-expressing fish by co-injection of atg-RTK1 morpholino (shaded bars, Panel G). Ctr-RTK2 and ctr-RTK1 were used as control. ANOVA and Bonferroni's multiple comparison tests were used for statistical analysis. Comparing axonal length in SOD1A4V fish injected with ctr-RTK2 (n=39) vs. different doses atg-RTK2: 3 ng (n=43, p=0.0059), 4.5 ng (n=37, p=0.0016, Panel D), SOD1G93A: ctr-RTK2 (n=60) vs. atg-RTK2: 1.5 ng (n=55, p=0.015), 3 ng (n=51, p=2.82×10-9), 4.5 ng (n=46, p=2.22×10-15, Panel E), SOD1G37R: ctr-RTK2 (n=37) vs. atg-RTK2: 3 ng (n=25, p=0.027), 4.5 ng (n=36, p=0.0018, Panel F) and SOD1A4V: ctr-RTK1 (n=49) vs. atg-RTK1: 1.5 ng (n=51, p=2.51×10-7), 3 ng (n=64, p=7.99×10-10), 4.5 ng (n=54, p<1×10-20, Panel G). Western blot of SOD1WT or SOD1A4V (1.76 ng) expressing zebrafish embryos (30 hpf), co-injected with either ctr-RTK1 or atg-RTK1 (4.5 ng). Sixty embryos were used per group with actin as the loading control (H). Immunostaining of rtk1 (green) in rhombomeres 3 and 5 and of ephrin-b2 (magenta) in rhombomere 4 in zebrafish embryos injected with either ctr-RTK1 or atg-RTK1 (4.5 ng). RTK1-depleted embryos show disorganized rhombomere boundaries (arrowhead, I, Scale bar 50 μm). Error bars are s.e.m.

This disclosure will be described with respect to particular embodiments and with reference to certain drawings, but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of this disclosure. Unless specifically defined herein, all terms used herein have the same meaning as they would to one skilled in the art of this disclosure. Practitioners are particularly directed to Sambrook et al., *Molecular Cloning: A Laboratory Manual*, 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

The term "EphA4" as used herein refers to a member of the ephrin (EPH) family. The ephrins and EPH-related receptors comprise the largest subfamily of receptor protein-tyrosine kinases and have been implicated in mediating developmental events, especially in the nervous system and in erythropoiesis. In vertebrates, there are ten EphA (nine in mammals) and six EphB receptors (five in mammals): EphA1-EphA10 (no EphA9 in mammals) and EphB1-EphB6 (no EphB5 in mammals). Based on their structures and sequence relationships, ephrins are divided into six ligands (five in mammals) of the ephrin-A (EFNA) class, which are anchored to the membrane by a glycosylphosphatidylinositol linkage, and three members of the ephrin-B (EFNB) class, which are transmembrane proteins (Pasquale, *Nature Neurosci.*, p. 417-418 (2004); Pasquale, *Nat. Rev. Mol. Cell Biol.* (2005), pp. 462-475; Pasquale, *Cell* (2008), 133(1):38-52). The Ephrin A4 receptor (Gene ID: 2043 in humans) binds ephrin-A ligands and, with lower affinity, ephrin-B1 and ephrin-B2 (Gene ID: 1948 in humans).

A distinctive feature of Eph-ephrin complexes is their ability to generate bidirectional signals that affect both the receptor-expressing and ephrin-expressing cells (Pasquale, *Cell* (2008), 133(1):38-52). Thus, an "inhibitor of EphA4 signaling," as used herein, is a functional inhibitor of the EphA4 receptor, either by targeting EphA4 directly, by targeting one or more of its ligands (e.g., ephrin-B2), one or more of its effector molecules (downstream of the receptor), or by targeting the interaction of EphA4 with these molecules. As mentioned, the EphA4 receptor binds all ephrin-A ligands, but also ephrin-B1 and ephrin-B2, and all of these may be inhibited. It is particularly envisaged that ephrin-B2 or the interaction between EphA4 and ephrin-B2 is targeted.

Eph receptors and ephrins use some common signaling effectors, such as Src family kinases and Ras/Rho family GTPases, which are particularly important for the organization of the actin cytoskeleton and cell adhesion (Pasquale, *Cell* (2008), 133(1):38-52), whereas the GTPase-activating proteins SPAR/E6TP1 interact only with EphA4 and EphA6 (Richter et al., *J. Neurosci.* 27 (2007), pp. 14205-14215). It is envisaged that the interaction between EphA4 and these effectors may be inhibited as well. As interaction between Eph receptors and ephrins requires cell-cell contact because both families are anchored to the plasma membrane, inhibitors of cell-cell contact may be envisaged as well.

The term "motor neuron disease," as used herein, refers to diseases that primarily (but not necessarily exclusively) affect motor neurons. These are systemic atrophies primarily affecting the central nervous system. Thus, "motor neuron disease," as used herein, refers to a disease of grey matter (as opposed to demyelinating diseases, which are white matter diseases). According to particular embodiments, the motor neuron disease is an anterior horn disease, i.e., a disease primarily affecting the anterior horn of the spinal cord, thus, the ventral (front) grey matter section of the spinal cord. The anterior horn diseases include amyotrophic lateral sclerosis, spinal muscular atrophy, Charcot-Marie-Tooth disease, poliomyelitis, West Nile virus, and progressive muscular atrophy. These motor neurons are also affected in Spinal and Bulbar Muscular Atrophy (Kennedy disease). According to particular embodiments, these motor neuron diseases are systemic diseases that fall under the G10-G13 block of the ICD-10 classification of the WHO. ICD-10 stands for the International Statistical Classification of Diseases and Related Health Problems, 10th Revision.

According to most particular embodiments, the motor neuron diseases are classified as a G12 disease in the ICD-10 classification. The G12 code groups spinal muscular atrophy and related syndromes, and includes Infantile spinal muscular atrophy, type I [Werdnig-Hoffman] (G12.0); Progressive bulbar palsy of childhood [Fazio-Londe]; Spinal muscular atrophy: adult form; childhood form, type II; distal; juvenile form, type III [Kugelberg-Welander]; scapuloperoneal form (i.e., other inherited spinal muscular atrophy, G12.1); Motor neuron disease (G12.2); Familial motor neuron disease; Lateral sclerosis: amyotrophic; Lateral sclerosis: primary; Progressive: bulbar palsy; Progressive: spinal muscular atrophy; other spinal muscular atrophies and related syndromes (G12.8); and Spinal muscular atrophy, unspecified (G12.9). Most particularly, the disease is selected from amyotrophic lateral sclerosis and spinal muscular atrophy.

Despite significant efforts, there are currently no satisfactory treatments for motor neuron diseases. Provided is a novel approach to ameliorate disease outcome in these syndromes.

Thus, according to a first aspect, an inhibitor of EphA4 signaling is provided for use in treatment of a motor neuron disease. "Treatment of a motor neuron disease," as used herein, does not necessarily imply a complete curative effect, but can also mean a disease-modifying effect, e.g., slowing down progression of the disease, delaying onset of the disease, prolonging survival after onset of the disease, improving motoric functions, etc.

As mentioned, the inhibitor of EphA4 signaling can target EphA4 itself, one or more of its ligands, one or more of its effector molecules, or target an interaction between these molecules. Inhibition can be at the genetic, transcriptional, translational or post-translational level and can be by targeting DNA, RNA, or protein (including interactions thereof, e.g., protein-protein interactions such as ligand-receptor interactions).

Inhibition at the genetic level, targeting DNA, can be by using gene therapy to knock out or reduce function of a gene. Inhibition at DNA level can also be done by using zinc finger nucleases (e.g., obtainable from Sigma), TAL effector nucleases (e.g., obtainable from Cellectis bioresearch) or meganucleases (e.g., obtainable from Cellectis bioresearch). RNA inhibition can be achieved, e.g., by using siRNA or miRNA. Inhibition at the protein level can be achieved, e.g., by using antibodies, nanobodies (Ablynx) or protein interference technology (WO2007/071789), or by the use of small molecules. The skilled person can readily think of further alternatives.

The way inhibition is achieved is not vital, as long as it results in a decrease in signaling. Such inhibition of EphA4 signaling suitably will be at least a 10% or 20% difference relative to a control, more preferably, at least a 30%, 40%, 50%, 60%, 70%, 80%, or 90% difference in signaling relative to a control. It will be particularly preferred where interaction or contact with an inhibitor results in complete or essentially complete inhibition of signaling relative to a control, e.g., at least about a 95%, 97%, 98%, 99% or 100% inhibition of signaling relative to control. A control sample for determination of such modulation can be comparable cells (in vitro or in vivo) that have not been contacted with the inhibitor. The monitoring of the % inhibition of EphA4 signaling can be followed, e.g., by measuring the axonal length, since this is inversely correlated with EphA4 signaling or, in case inhibition is achieved by inhibiting expression of EphA4 or one of its interacting proteins, by measuring the remaining expression of the protein whose expression is inhibited. Inhibition of signaling can also be achieved by inhibition of autophosphorylation. Inhibition of signaling can also be achieved by inhibition of expression of a relevant target. The same considerations in % difference to a control apply, mutatis mutandis.

As EphA4 is important for axon guidance during development, partial inhibition of EphA4 is also envisaged. Indeed, while EphA4 knockout mice display a motoric phenotype, heterozygous EphA4 mice do not (see example section).

Inhibitors of EphA4 have been described before. WO2004/028551 describes three 12-amino acid peptides that preferentially bind to EphA4, i.e., KYLPYWPVLSSL (SEQ ID NO:1, referred to as the KYL peptide), APYCVYRGSWSC (SEQ ID NO:2, referred to as the APY peptide) and VTMEAINLAFPG (SEQ ID NO:3, referred to as the VTM peptide).

Interestingly, although it is shown in WO2004/028551 that these peptides are antagonists of EphA4 signaling (see, e.g., FIGS. 15-17 therein), it is also suggested that administering an agonist of ephrin receptor signaling is desirable to promote neuronal regeneration (see summary of invention section in WO2004/028551), and not an antagonist. This is in line with other reports that state that decrease of EphA4, which is a gamma-secretase substrate, precedes memory decline in Alzheimer disease (Simon et al., *J. Alzheimers Dis.* (2009), 17(4):773-86). Note that, in view of its role in developmental axon guidance, the role of EphA4 in neuronal regeneration after spinal cord injury has been studied. However, as at least two independent groups found no regeneration upon EphA4 inhibition (Cruz-Orengo et al., *Neurosci. Lett.* (2007), 418(1): 49-54) or no prevention of astroglial-fibrotic scar formation after spinal cord injury in EphA4-deficient mice (Herrmann et al., *Exp. Neurol.* (2010 June), 223(2):582-98), it appears that the role of EphA4 cannot just be extrapolated and should be evaluated for every disease setting.

Other EphA4 inhibitors have been proposed by Noberini et al.[10] These are two isomeric small molecule 2,5-dimethylpyrrolyl benzoic acid derivatives that selectively inhibit ephrin binding to EphA4 (compound 1 and 2, respectively, see figure below).

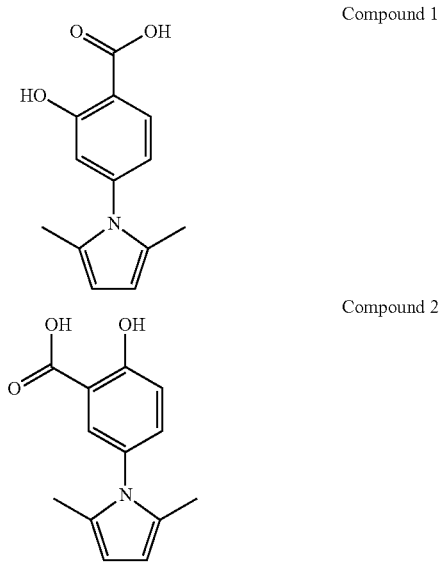

Compound 1

Compound 2

Further inhibitors are unclustered ephrin-A5-Fc and EphA4-Fc, as described in reference 33 (Goldshmit et al., 2011). Other references describing small molecule inhibitors are, e.g., Van Linden et al., *Eur. J. Med. Chem.* (2012), 47(1): 493-500; and Parmentier-Batteur et al., *J. Neurochem.* (2011), 118(6):1016-31.

EphA4 antibodies are commercially available (e.g., Santa Cruz, Invitrogen), however, to our knowledge, these have not yet been tested for inhibitory capacity. Nevertheless, it is within the capabilities of the skilled person to make and select inhibitory antibodies using established techniques. Likewise, inhibitory nanobodies can be made.

According to particular embodiments, the inhibitor of EphA4 signaling is selected from a peptide, a 2,5-dimethylpyrrolyl benzoic acid derivative, a nanobody, ephrin-A5-Fc and EphA4-Fc. According to further particular embodiments, the inhibitor is selected from the KYL, APY or VTM peptide, compound 1 or 2, an inhibitory nanobody against EphA4, or unclustered ephrin-A5-Fc and EphA4-Fc. According to further particular embodiments, the inhibitor of EphA4 signaling is selected from the KYL peptide, compound 1 or 2, or unclustered ephrin-A5-Fc and EphA4-Fc. According to yet further particular embodiments, the inhibitor of EphA4 signaling is selected from the KYL peptide or compound 1 or 2.

Accordingly, methods for treating a motor neuron disease in a subject in need thereof are provided, comprising administering an inhibitor of EphA4 signaling to the subject.

As the motor neuron disease affects the neurons in the anterior horn of the spinal cord, intrathecal administration of the EphA4 inhibitor is particularly envisaged.

In a further aspect, EphA4 can be used as a (prognostic) biomarker for motor neuron disease. Particularly, it was found that EphA4 levels (or activity, particularly tyrosine autophosphorylation activity) inversely correlate with disease onset and with disease duration (or survival in case of lethal disease). Here also, the biomarkers for motor neuron diseases are typically for diseases of grey matter that directly affect motor neurons. According to particular embodiments, the motor neuron diseases envisaged are G12 diseases in the ICD-10 classification of the WHO. According to alternative embodiments, the motor neuron diseases are anterior horn diseases. Most particularly, envisaged diseases for treatment are amyotrophic lateral sclerosis (ALS) and spinal muscular atrophy (SMA). ALS can be sporadic ALS or familial ALS.

Accordingly, methods are provided to determine onset or progression of a motor neuron disease in a subject, comprising determining EphA4 levels and/or EphA4 activity in a sample of the subject. According to further specific embodiments, decreased EphA4 levels and/or activity are indicative of delayed onset (in a subject at risk of developing a motor neuron disease) and/or increased survival (or disease duration). Determining decreased levels typically means decreased compared to control. As with inhibition, decreased levels of EphA4 levels or activity (e.g., signaling) suitably will be at least a 10% or 20% difference relative to a control, more preferably, at least a 30%, 40%, 50%, 60%, 70%, 80%, or 90% difference in expression levels or signaling activity relative to a control. The other considerations for inhibition apply mutatis mutandis.

Ways in which expression levels are measured are known to the skilled person, and can be done at, e.g., the protein or mRNA level; the exact methodology is not vital to the disclosure. Decrease is typically measured quantitatively, but can also be qualitatively, e.g., in case of absence of expression. Although EphA4 levels can be measured at the protein level (e.g., using anti-EphA4 antibody in Western blot or Elisa), it is particularly envisaged that EphA4 expression and/or activity is measured at the mRNA level.

According to particular embodiments, EphA4 levels and/or activity are measured using quantitative PCR.

According to particular embodiments, EphA4 levels and/or activity may be measured by assessing presence of a mutation in the EphA4 protein or mRNA. Particularly envisaged mutations include the R514X mutation (which truncates the protein, leading to decreased levels or absence of EphA4) or the R571Q mutation (which interferes with autophosphorylation activity, yielding an inactive EphA4 protein). For specific mutations, like the two mentioned, it is known that they correlate with decreased expression or activity, so the qualitative determination of the presence of the mutation is equivalent to the quantitative determination of decreased expression or activity.

Decreased activity or signaling can suitably be determined by the skilled person, e.g., using in vitro or cellular experiments with a suitably labeled reporter gene. Another way this can be determined is by determining autophosphorylation of EphA4, as this is required for its signaling activity; a decrease in autophosphorylation corresponds to a decrease in signaling.

The biomarker can be used as a prognosis to predict disease onset, or can be used to make predictions about disease progression. Predicting disease onset will typically be done in patients at risk of developing a motor neuron disease, e.g., in cases of familial motor neuron disease, such as familial ALS.

Disease progression can be monitored or predicted in any subject having a motor neuron disease, and it is shown herein that lower EphA4 levels and/or activity are indicative of prolonged survival (or disease duration).

Also, the biomarker can be used to monitor response to therapy. In the latter case, decrease of EphA4 levels and/or activity indicates that the patient will have increased disease duration or survival. For instance, when EphA4 inhibition is used as therapy, monitoring EphA4 levels will yield an indication of the success of the therapy.

According to a further aspect, methods of screening compounds for inhibitory capacity on EphA4 signaling are provided. "Compounds" as used herein may refer to chemical compounds (e.g., small molecules), nucleic acid compounds (e.g., siRNA), proteins (e.g., antibodies) or synthetic analogues of such compounds (e.g., LNA, PNA, morpholine).

One example of such screening methods is the screening in an animal model, particularly a zebrafish model. The model is typically a model of motor neuron disease, such as an ALS or SMA model. Thus, screening methods are provided, comprising:

administering a compound of interest to an animal that has a motor neuron disease; and evaluating the inhibitory effect on EphA4 signaling by evaluating at least one parameter of the phenotype of the motor neuron disease in the animal.

EphA4 signaling is inversely correlated with improvement of the phenotype. Thus, improvement of a parameter is indicative of inhibitory effect on EphA4 signaling. A typical parameter that can be evaluated is axon length. Survival can also be used as a parameter. Other parameters are shown in the examples. Alternatively, if the compound is expected to interfere with expression of EphA4 or one of its interaction partners, expression of that protein can be used as alternative or additional parameter to evaluate the inhibitory effect (i.e., a decrease in EphA4 expression indicates a decrease in EphA4 signaling; the same goes for decreased expression of EphA4 ligands or effector molecules).

As mentioned, it is particularly envisaged to use a zebrafish model for motor neuron disease. Zebrafish are easier to screen compounds in than mice and have the added advantage that compounds can often be directly added to the water. Moreover, there are good zebrafish models for motor neuron disease, e.g., mutant SOD1 axonopathy (reference 13, model for ALS), mutant TDP-43 axonopathy (reference 14, model for ALS), SMN loss (reference 15, model for SMA). These models are particularly envisaged for use in the methods.

The screening methods may comprise a further step wherein the result is compared to a control. Controls may be control compounds (both positive and negative) or control animals (e.g., animals without motor neuron disease, to evaluate potential adverse effects).

It is to be understood that although particular embodiments, specific configurations as well as materials and/or molecules, have been discussed herein for cells and methods according to this disclosure, various changes or modifications in form and detail may be made without departing from the scope and spirit hereof. The following examples are provided to better illustrate particular embodiments, and they should not be considered limiting the application.

EXAMPLES

Example 1

EphA4 Knockdown Rescues the Mutant SOD1-Induced Motor Axonopathy

Figure 2:
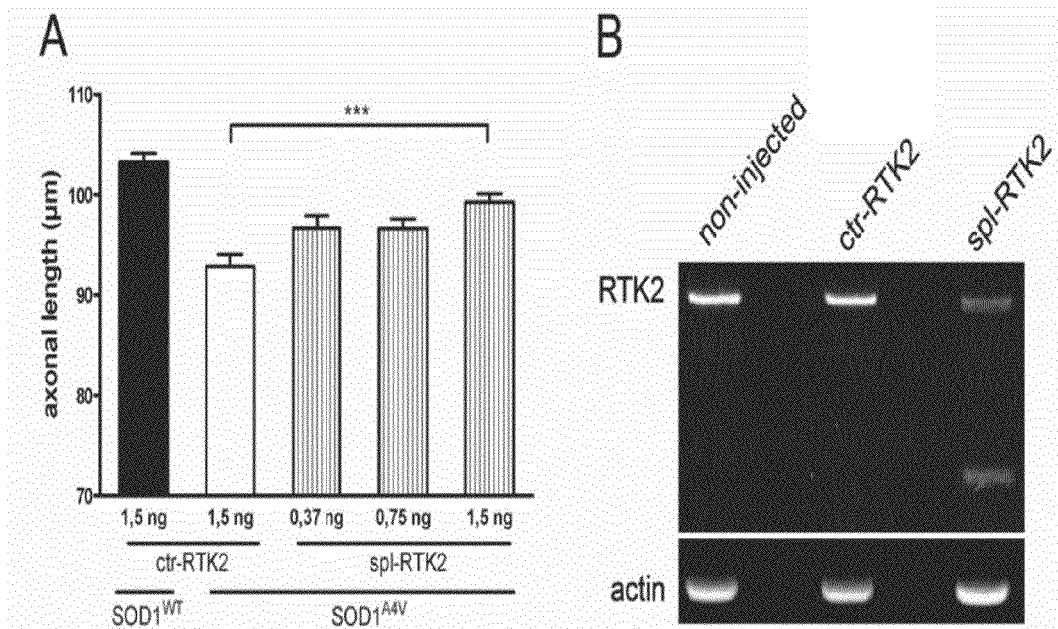
FIG. 2: RTK2 knockdown protects motor axons against $SOD1^{A4V}$-induced injury. Effect of RTK2 knockdown, established by injection of splice-rtk2 morpholino, on the motor axon length of $SOD1^{A4V}$-expressing zebrafish embryos (30 hpf). $SOD1^{WT}$-expressing fish and a non-functional five-base pair-mismatch control morpholino (ctr-RTK2) were used as control (Panel A). ANOVA and Bonferroni's multiple comparison tests were used for statistical analysis: $SOD1^{A4V}$/ctr-RTK2 (n=56) vs. $SOD1^{A4V}$/spl-RTK2 (n=60, 1.79×10$^{-4}$). Spl-RTK2 was designed against the exon 2 splice site of the zebrafish RTK2 pre-mRNA and alternatively skipped out exon 2. RT-PCR on non-transgenic fish (lane 1), ctr-RTK2-injected fish (lane 2) and spl-RTK2-injected fish (lane 3) at 30 hpf. Functional RTK2 mRNA, containing exon 2, is indicated by the 818-bp product (upper band) while non-functional RTK2 mRNA, lacking exon 2 is indicated by the 156-bp product (lower band), 60 embryos each group (Panel B). Error bars are s.e.m.
Figure 3:
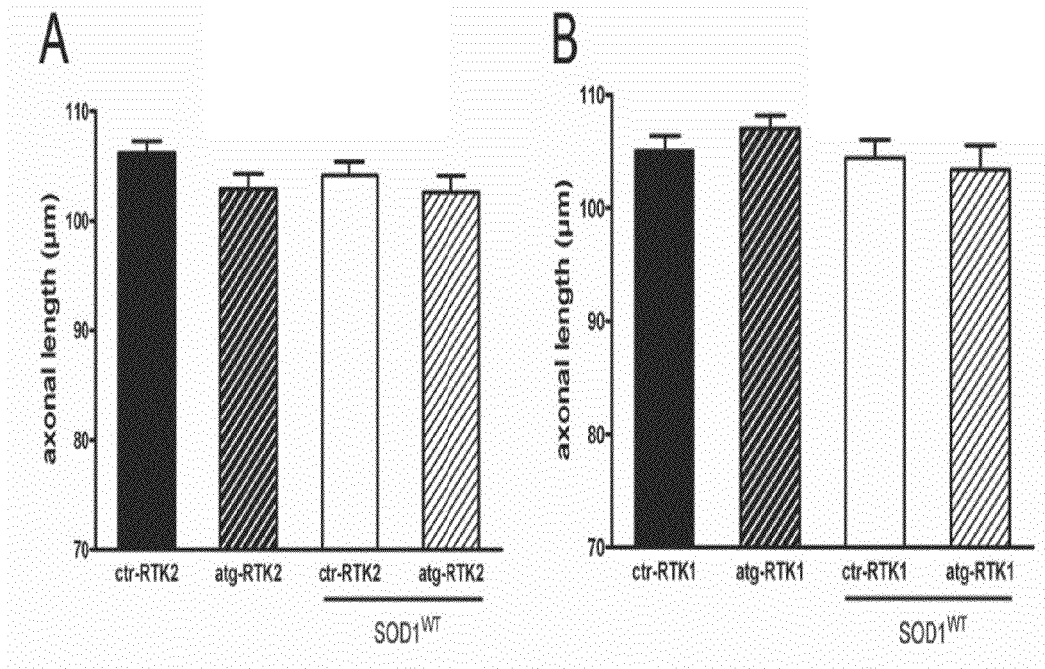
FIG. 3: EphA4 knockdown does not alter the motor axonal length in non-transgenic or wild-type SOD1 fish. Y-axes show motor axon length of non-transgenic (black bar) or SOD1WT-expressing (white bar) zebrafish embryos, injected with either atg-RTK2 (shaded bars, Panel A) or atg-RTK1 morpholino (shaded bars, Panel B). Ctr-RTK2 and ctr-RTK1 were used as controls. Error bars are s.e.m.

To identify disease-modifying genes in ALS in an unbiased way, knockdown screening was performed in the mutant SOD1 zebrafish model (reference 13), using a library of 303 translation blocking morpholinos (atg-mo), of which 58 were targeting genes presumed to be neuronally expressed (according to the NCBI database) and 245 randomly chosen targeting genes. Thirteen morpholinos out of 303 were found to rescue the mutant SOD1-induced axonopathy in the zebrafish (Table 1). The morpholino yielding the highest rescue in two separate experiments was studied further. It targets zebrafish receptor tyrosine kinase 2 (RTK2, also known as epha4b), which has 67% identity and 80% homology to the human orthologue EPHA4. Knockdown of RTK2 in fish expressing mutant SOD1 completely and dose-dependently rescued the motor axonopathy (both axonal length and aberrant branching) caused by three different SOD1 mutations: A4V, G93A and G37R (FIG. 1, Panels A-F; Table 2). The specificity of the effect of this atg-RTK2 morpholino was confirmed by replicating the protective effect of RTK2 knockdown using a splice-blocking morpholino (spl-RTK2) (FIG. 2, Panel A, and Table 3). Effectiveness of the spl-RTK2 morpholino was demonstrated using RT-PCR (FIG. 2, Panel B). Receptor tyrosine kinase 1 (RTK1, also known as epha4a), the fish paralogue of RTK2, has 83% identity and 92% homology to human EPHA4. RTK1 knockdown was dose-dependently and equally protective as RTK2 knockdown (FIG. 1, Panel G; Table 4). Atg-RTK1 efficiently blocked RTK1 expression as was demonstrated by Western blot of zebrafish embryos and whole-mount immunostaining of the rhombomeres, in which EphA4 is expressed abundantly (FIG. 1, Panels H, I). As previously described, disorganized rhombomere boundaries in RTK1-depleted embryos[16-17] was observed. At the doses used, the protective effect of this morpholino on the axonopathy induced by mutant SOD1 appeared specific, and not secondary to a general outgrowth stimulating action, as none of the morpholinos affected axonal or total body length in non-transgenic or wild-type SOD1-expressing fish (FIG. 3 and body length: ctr-RTK2: 2.73±0.02 mm, n=29, vs. atg-RTK2: 2.70±0.01 mm, n=32; ctr-RTK1: 2.62±0.01 mm, n=20, vs. atg-RTK1: 2.61±0.01 mm, n=30).

Example 2

EphA4 Deletion Attenuates Motor Neuron Degeneration in Mutant SOD1 Mice

The EphA4 receptor is a member of the A subclass of Eph receptor tyrosine kinases, and interacts with both A-type and B-type ephrins. Signaling can take place in the receptor-expressing cell (forward signaling) and the ligand-expressing cell (retrograde signaling). In the developing nervous system, the ephrin family is involved in axonal repulsion and a key player in the establishment of topographical maps. In the adult nervous system, it has been implicated in synapse formation and the regulation of long-term synaptic plasticity and memory.[18]

Figure 4:
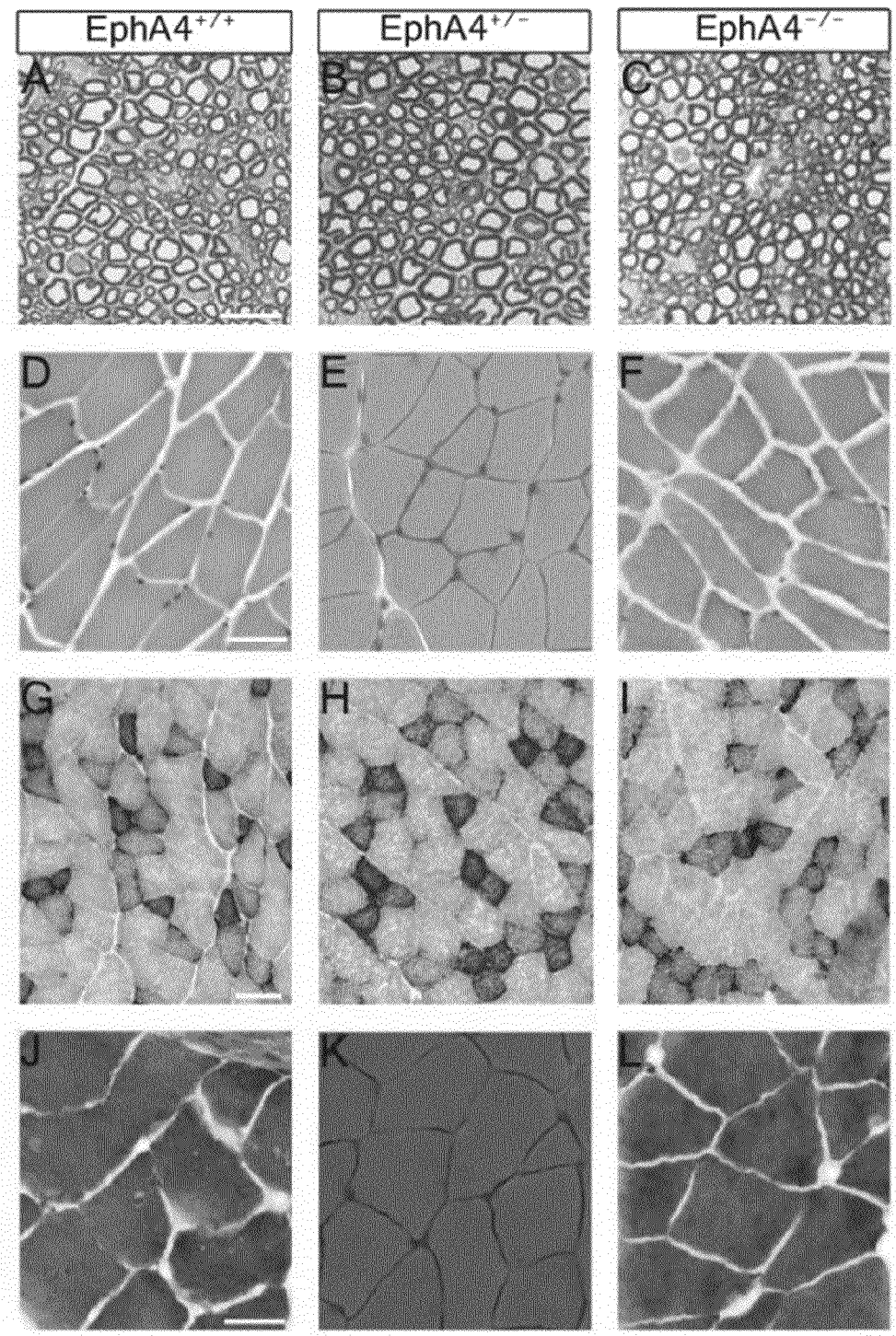
FIG. 4: Ventral horn motor neurons and their projections to the musculature are normal in EphA4+/− and EphA4−/− mice. Morphology and proportion of small and large sciatic nerve axons (Panels A-C; scale 20 μm), gastrocnemius muscle morphology: hematoxilin/eosin staining (Panels D-F), NADH-staining (Panels G-I) and gommori staining (Panels J-L) (scale 50 μm), the proportion innervated, partial denervated or denervated neuromuscular junctions (Panels M, N; scale 20 μm) and the total number of ventral horn motor neurons or the distribution according to motor neuron cell body area (μm$^2$) (Panels O, P; scale 100 μm) of 140-day-old EphA4$^{−/−}$ mice (n=3), EphA4$^{+/−}$ mice (n=3) and non-transgenic littermate controls (EphA4$^{+/+}$, n=3). Error bars are s.e.m.
Figure 4:
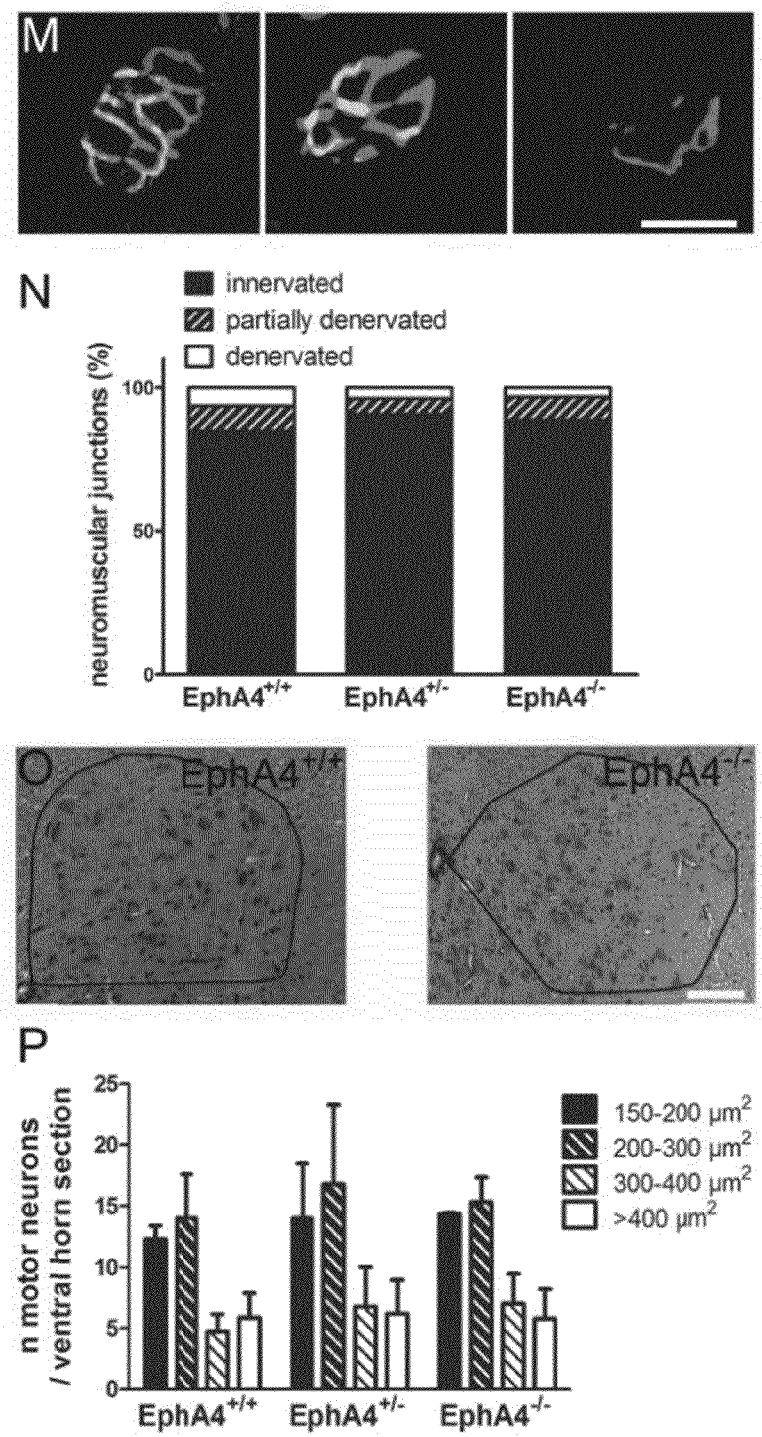
Figure 5:
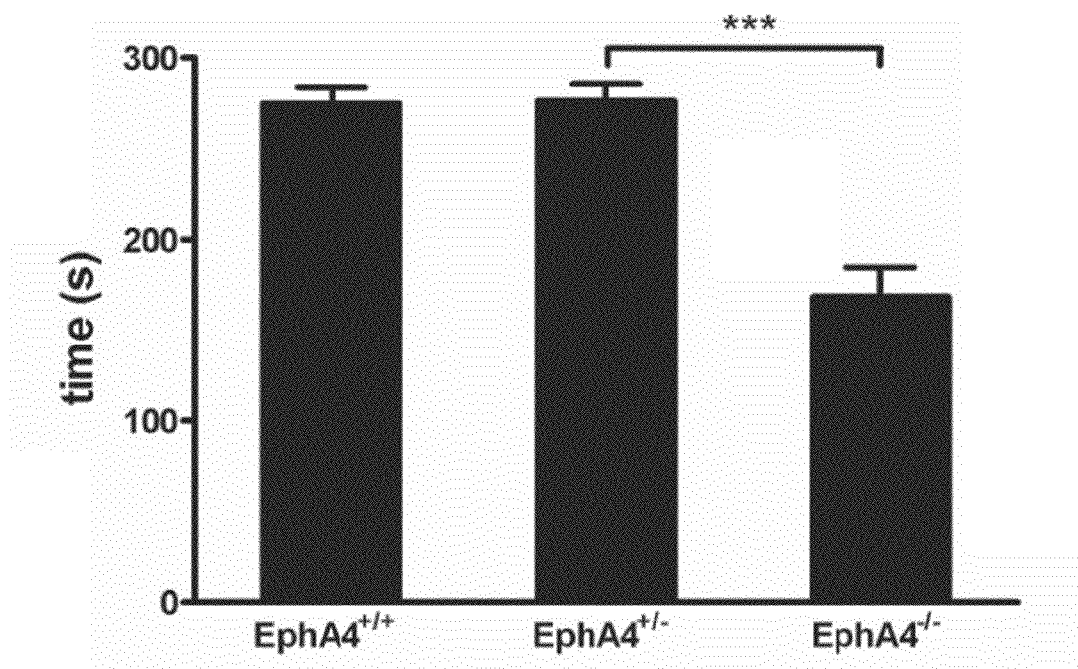
FIG. 5: EphA4−/− mice have poor rotarod performance compared to their littermate controls. Rotarod performance of EphA4 knockout mice (EphA4$^{−/−}$, n=7) compared to their heterozygous (EphA4$^{+/−}$, n=15) and non-transgenic (EphA4$^{+/+}$, n=24) littermate controls (ANOVA, p=1.44×10$^{−6}$). Error bars are s.e.m.
Figure 6:
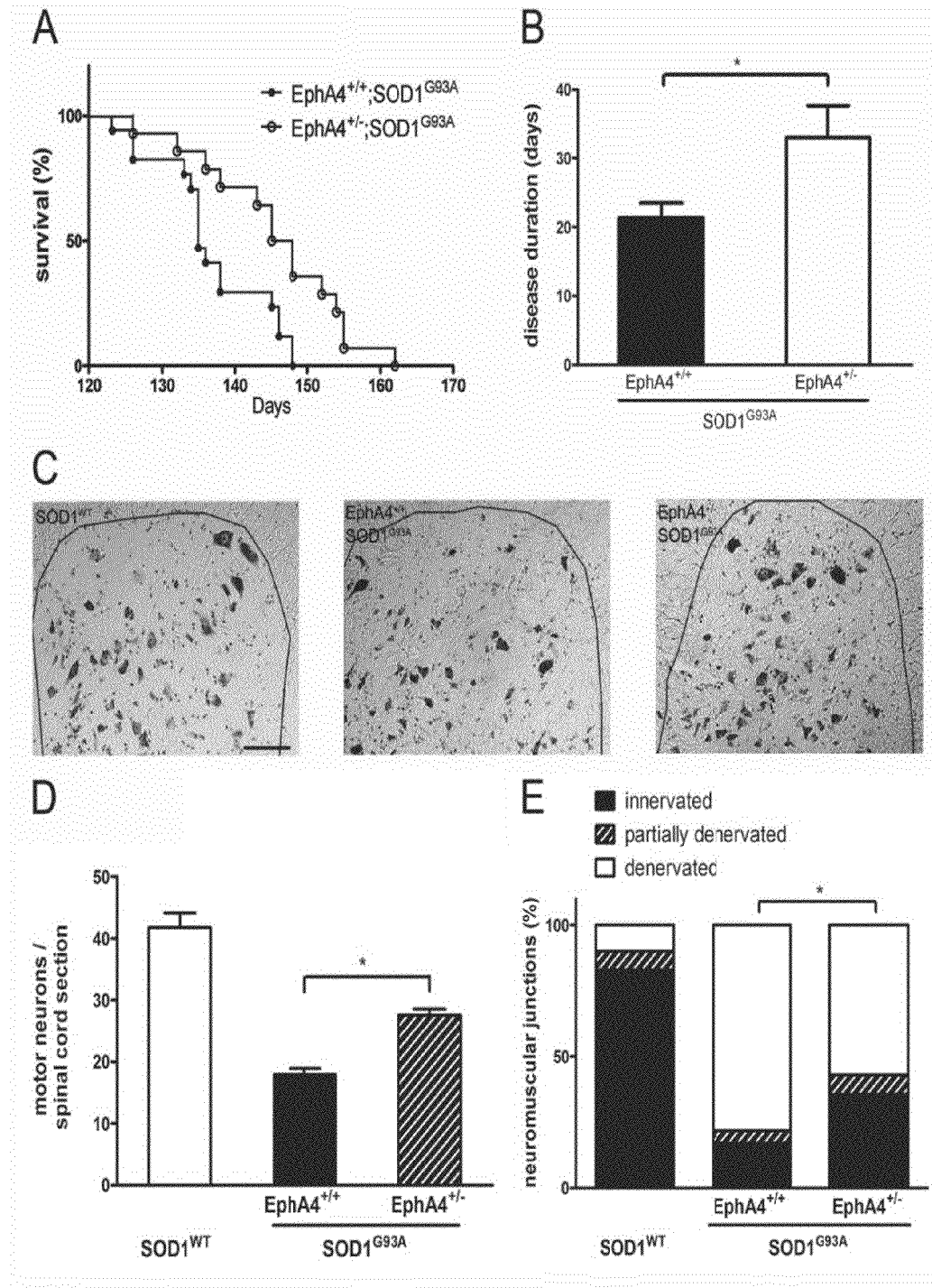
FIG. 6: EphA4 deletion slows disease progression in SOD1$^{G93A}$ mice. Survival analysis of SOD 1$^{G93A}$ mice in EphA4$^{+/+}$ or EphA4$^{+/−}$ background. Median survival: 146.5 days (EphA4$^{+/−}$;SOD1$^{G93A}$, n=14) versus 135 days (EphA4$^{+/+}$;SOD1$^{G93A}$, n=17, Log Rank p=0.0063, Panel A). Average disease duration: 33 days (EphA4$^{+/−}$;SOD1$^{G93A}$, n=13) versus 21 days (EphA4$^{+/+}$;SOD1$^{G93A}$, n=15, T-test p=0.026, Panel B). Females and males were equally proportioned in both groups (EphA4$^{+/+}$;SOD1$^{G93A}$: 41% females and EphA4$^{+/-}$;SOD1$^{G93A}$: 43% females). Quantification of intact ventral horn motor neurons (Panels C, D) and completely innervated neuromuscular junctions (Panel E) in late-symptomatic SOD1$^{G93A}$ mice. Amount of ventral horn motor neurons: 27.57+/−7.19 (EphA4$^{+/-}$;SOD1$^{G93A}$, n=9) versus 17.89+/−7.54 (EphA4$^{+/+}$;SOD1$^{G93A}$, n=9, age-matched littermate controlled, ANOVA, p=1.69×10$^{-2}$, scale 100 μm). Percentage completely innervated neuromuscular junctions: 35.70% (842/2395, EphA4$^{+/-}$;SOD1$^{G93A}$, n=9) versus 17.26% (588/3313, EphA4$^{+/+}$;SOD1$^{G93A}$, n=9, age-matched littermate controlled, OR=2.51+/−[2.22-2.85], p<1×10$^{-20}$). Error bars are s.e.m.
Figure 7:
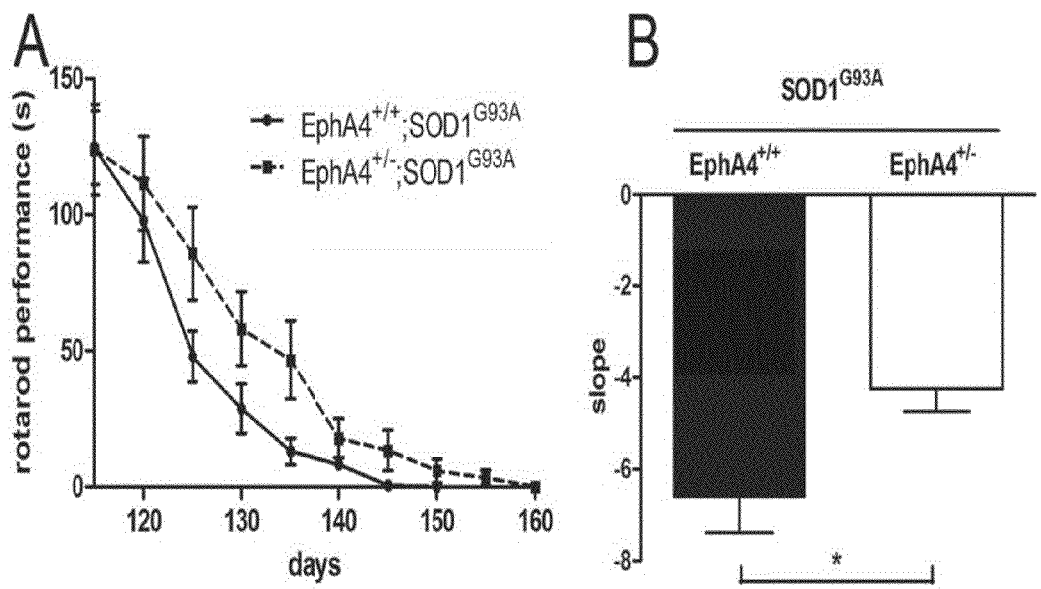
FIG. 7: EphA4 depletion slows progression after disease onset in SOD1G93A mice. Accelerating rotarod performance of EphA4$^{+/+}$;SOD1$^{G93A}$ mice (n=15) and EphA4$^{+/-}$;SOD1$^{G93A}$ mice (n=13) (Panel A). T-test was used to compare average slopes: −6.60+/−0.79 (EphA4$^{+/+}$;SOD1$^{G93A}$) versus −4.25+/−0.50 (EphA4$^{+/-}$;SOD1$^{G93A}$, p=0.022, Panel B). Error bars are s.e.m.

To assess the effect of EphA4 gene deletion in the SOD1$^{G93A}$ mouse, SOD1$^{G93A}$ mice were cross-bred with EphA4 knockout (EphA4$^{-/-}$) mice. The EphA4$^{-/-}$ mouse was described previously and develops an abnormal "hopping gait" due to miswiring of the central pattern generators.[19] Deletion of the EphA4 gene gives rise to abnormal projections of neuronal tracts such as the corticospinal tract, the anterior commisure and the reticulospinal tract.[20] Ventral horn neurons and their projections to the muscle were normal in EphA4$^{+/-}$ and EphA4$^{-/-}$ mice (FIG. 4). EphA4$^{-/-}$ mice younger than 6 weeks of age had a decreased body weight compared to their littermate controls [16.95 g+/−0.57 (EphA4$^{-/-}$, n=10) versus 20.05 g+/−0.60 (EphA4$^{+/-}$, n=12, p=2.51×10$^{-3}$) and 21.16 g+/−0.72 (EphA4$^{-/-}$, n=6, p=2.81×10)] and developed a severe hopping gait as described before.[20] This significantly impaired their performance on the rotarod, which precluded studying motor performance of double transgenic EphA4$^{-/-}$;SOD1$^{G93A}$ mice. In addition, the number of EphA4 knockout mice born was remarkably lower than expected based upon a Mendelian distribution (Table 5); hence, almost no EphA4$^{-/-}$;SOD1$^{G93A}$ mice were obtained. Therefore, SOD1$^{G93A}$ mice heterozygous for the EphA4 gene deletion (EphA4$^{+/-}$;SOD1$^{G93A}$) were studied. Interestingly, even deletion of only one EphA4 allele in the SOD1G93A mouse significantly increased motor performance and survival (FIG. 6, Panels A, B and FIG. 7). Disease onset assessed by rotarod performance was not affected. In addition, ventral horn motor neurons (FIG. 6, Panels C, D) and neuromuscular junctions (FIG. 6, Panel E) were maintained longer as compared to age-matched controls (EphA4$^{+/+}$;SOD1$^{G93A}$), indicating that deletion of one EphA4 allele slows motor neuron degeneration in the SOD1$^{G93A}$ mouse model.

Example 3

Vulnerable Motor Neurons have High Expression Levels of EphA4

Figure 8:
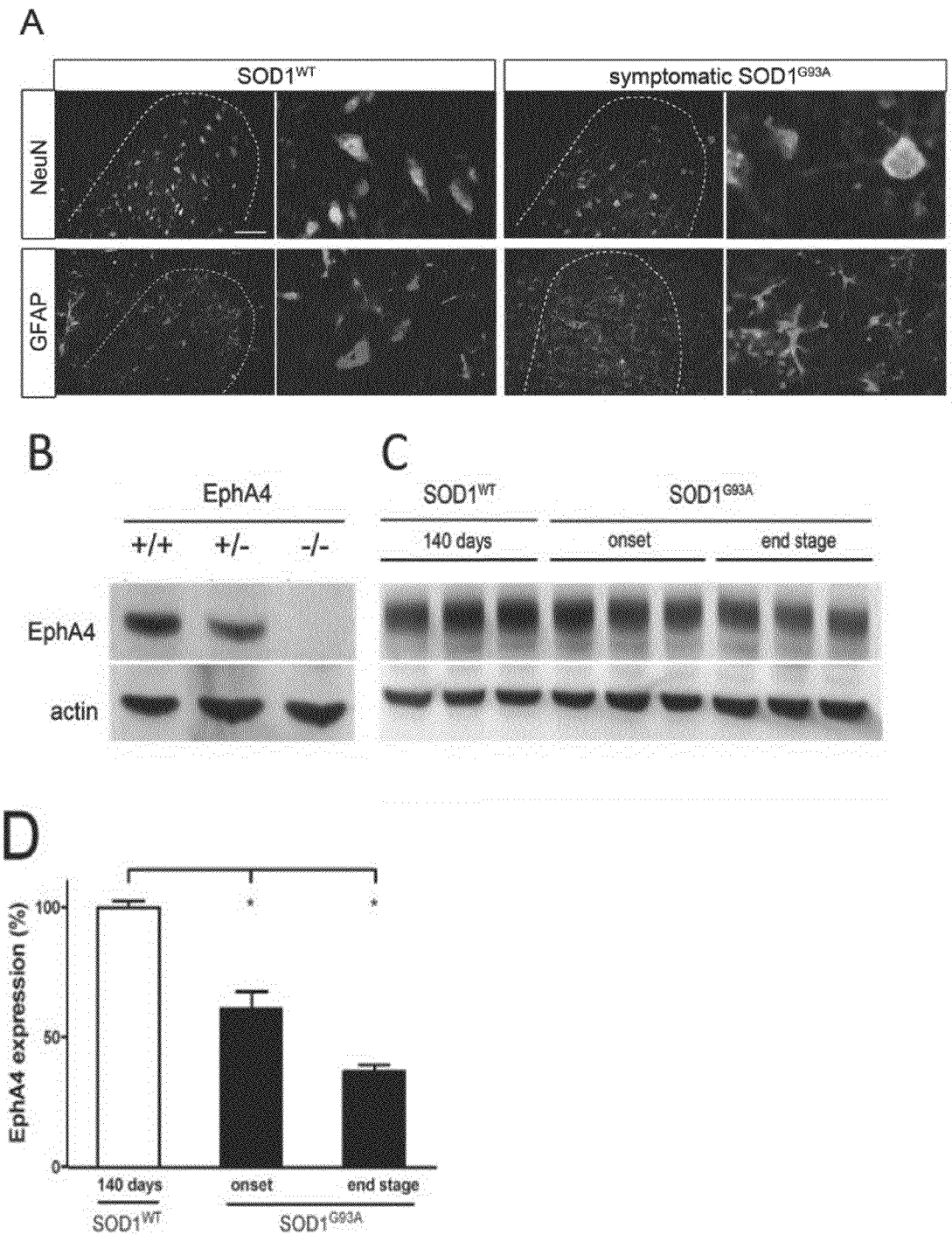
FIG. 8: EphA4 expression declines during disease progression. Immunostaining of EphA4 (magenta) in the spinal cord of SOD1$^{WT}$ (left) and late-symptomatic SOD1$^{G93A}$ mice (right). Co-labeling was performed with the neuronal marker NeuN (green, upper panels) and with the astrocytic marker GFAP (green, lower panels). Dotted line surrounds the ventral horn, scale 100 μm (Panel A). Antibody specificity was shown by Western blot of spinal cords of 130-day-old non-transgenic (EphA4$^{+/+}$), EphA4 heterozygous (EphA4$^{+/-}$) and full knockout (EphA4$^{-/-}$) mice (Panel B). Western blot of spinal cords of SOD1$^{WT}$ mice (140 days old, n=3, 100% expression) and SOD mice at disease onset (n=3, 61% expression) and at end stage (n=3, 37% expression, ANOVA, p=0.0027). Actin was used as loading control (Panels B, C).
Figure 9:
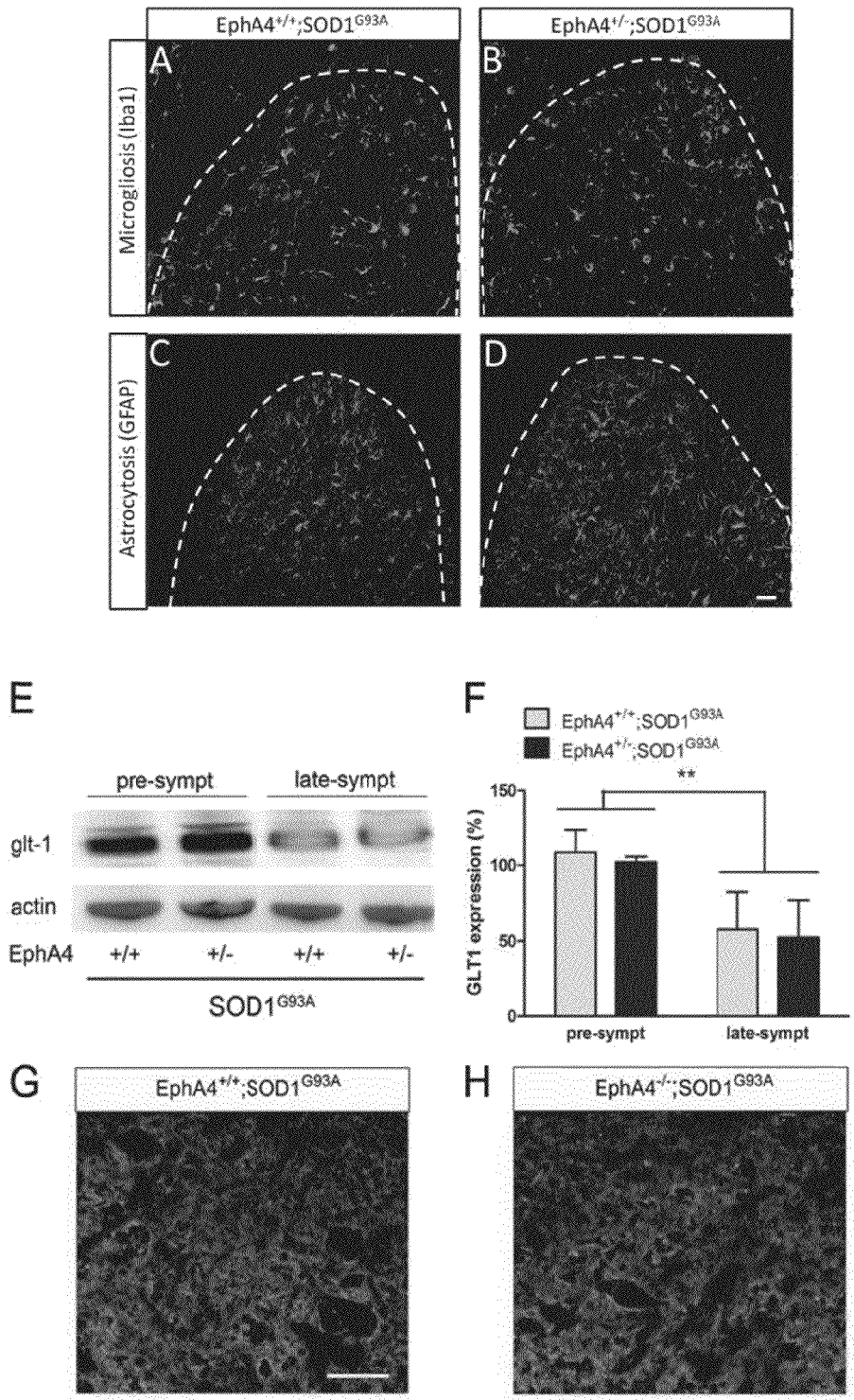
FIG. 9: EphA4 levels do not correlate with gliosis or GLT1 expression in SOD1G93A mice. Immunostaining of lumbal spinal cords of disease-matched symptomatic EphA4$^{+/+}$; SOD1$^{G93A}$ (Panels A, C) and EphA4$^{+/-}$;SOD1$^{G93A}$ mice (Panels B, D) for the microglial marker Iba1 (Panels A, B) and for the astrocytic marker GFAP (Panels C, D). Scale 50 μm. GLT-1 expression declines during disease progression in spinal cords of SOD1$^{G93A}$ mice, disregarding expression levels of EphA4 (2-way ANOVA: $p_{genotype}$=0.60, $p_{disease\ stage}$=0.0018, $p_{genotype*disease\ stage}$=0.96, n=3, Panels E, F). At late-symptomatic stages, EphA4$^{-/-}$;SOD1$^{G93A}$ mice (Panel G) do not show altered GLT-1 expression compared to EphA4$^{+/+}$; SOD1$^{G93A}$ age-matched littermate controls, Scale 50 μm (H). Error bars are s.e.m.

To explore the mechanism through which reduced EphA4 expression is protective in ALS, the EphA4 expression profile was studied in spinal cords of wild-type SOD 1 and mutant SOD1 mice. EphA4 immunoreactivity was present in neurons as shown by its colocalization with the neuronal marker NeuN. Expression of EphA4 in the spinal cord decreased during disease progression (FIG. 8). No expression of EphA4 was found in astrocytes, identified by staining for GFAP (FIG. 8), or microglia, identified by staining for Iba1 (not shown). Unlike the findings in acute spinal cord injury models in which EphA4 is abundantly expressed by reactive astrocytes and even a regulator of glial activation,[21] EphA4 deletion did not modulate gliosis in mutant SOD1 mice (FIG. 9).

The EphA4 receptor has recently also been implicated in synaptic plasticity and long term potentiation in the adult hippocampus through down-regulation of the glial glutamate scavenger GLT-1, resulting in enhanced glutamatergic transmission.[22] Loss of GLT-1 resulting in glutamate-induced excitotoxic motor neuron death is thought to be a pathogenic mechanism in ALS.[23, 24] Therefore, the hypothesis reached was that the protective effect of blocking the EphA4 receptor may be mediated by up-regulation of GLT-1. To investigate this, spinal cord GLT-1 expression between heterozygous ALS (EphA4$^{+/-}$;SOD1$^{G93A}$) and SOD1$^{G93A}$ mice (EphA4$^{+/+}$; SOD1$^{G93A}$) was compared. As expected, GLT-1 expression decreased during disease progression in SOD1$^{G93A}$ animals. Deletion of one EphA4 allele did not result in an increased GLT-1 expression (FIG. 9, Panels E and F). In addition, staining of GLT-1 in the spinal cord did not show increased expression in general or in the vicinity of the motor neurons, not even in homozygous ALS mice (EphA4$^{-/-}$;SOD1$^{G93A}$, FIG. 9, Panels G and H). These observations make a contribution of the transporter to the survival benefit observed unlikely, particularly in view of the observation that a substantial increase of GLT-1 expression is necessary to result in even a small benefit on disease phenotype.[25,26]

Figure 10:
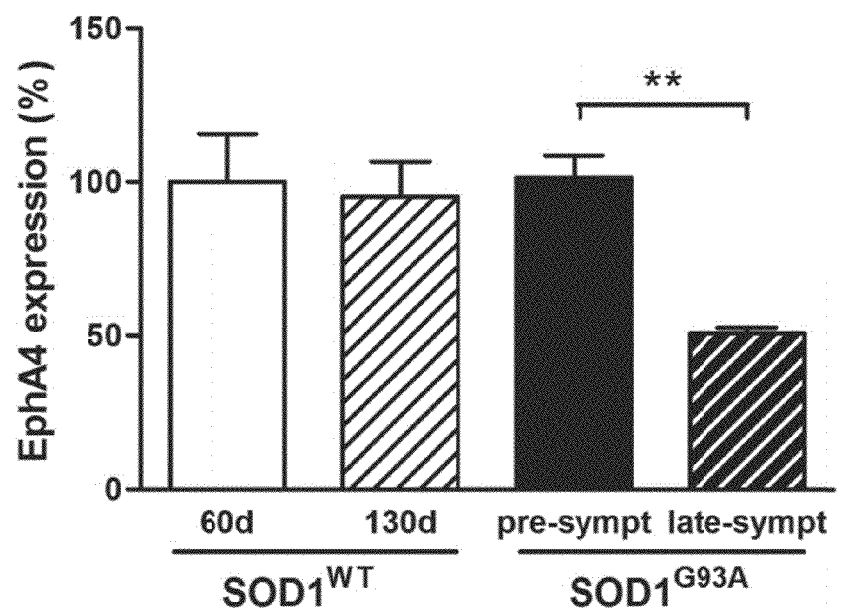
FIG. 10: Resistant motor neurons in late-symptomatic SOD1G93A mice have lower EphA4 levels. EphA4 expression in ventral horn (motor) neurons in the lumbal spinal cord of pre-symptomatic and late-symptomatic SOD 1$^{G93A}$ mice and age-matched nontransgenic controls, dissected using laser captures microscopy. Ventral horn (motor) neurons of late-symptomatic SOD1$^{G93A}$ mice show 50 percent lower EphA4 expression than neurons of pre-symptomatic SOD 1$^{G93A}$ mice (ANOVA p=0.0033, n=3). Polr2a was used as internal control. Error bars are s.e.m.
Figure 11:
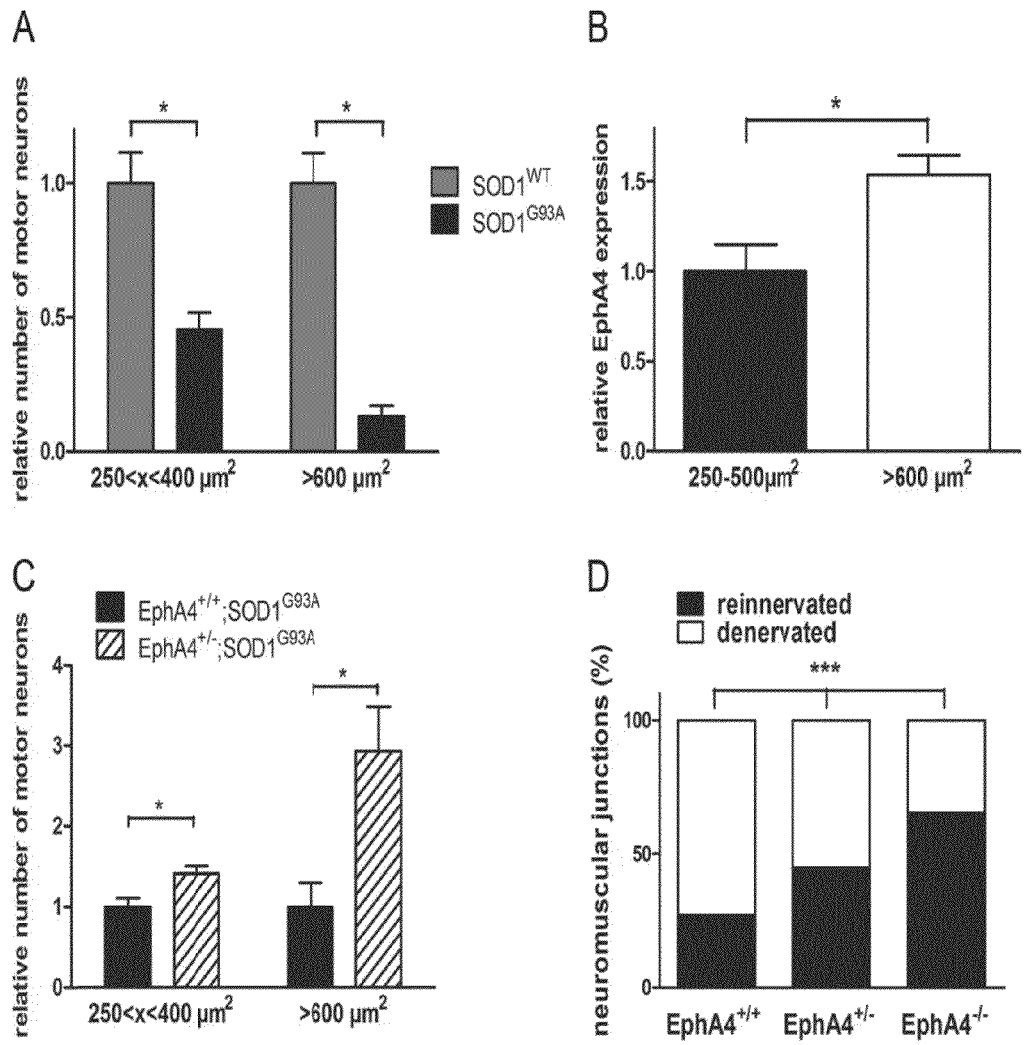
FIG. 11: Vulnerable motor neurons in ALS have higher expression levels of EphA4. Percentage small (250-600 μm$^2$) and large (>600 μm$^2$) motor neurons left in the ventral horn of the spinal cord of late-symptomatic SOD 1$^{G93A}$ mice (n=9) compared to 130-day-old SOD1$^{WT}$ controls (n=6). Large motor neurons are more vulnerable in the SOD 1$^{G93A}$ mouse model for ALS with 87 percent loss of large motor neurons versus 54 percent loss of small motor neurons (two-way ANOVA, $p_{genotype*motor\ neuron\ size}$=0.018, Panel A). Relative EphA4 expression in small and large motor neurons of non-transgenic mice dissected through laser capture microscopy. Large motor neurons have higher levels of EphA4 than small motor neurons (small motor neurons: 1.0+/−0.15, n=3 versus large motor neurons 1.54+/−0.11, n=3, t-test, p=0.044, at least 1500 neurons were dissected for each group). Polr2a was applied as internal control (Panel B). Relative number of small and large motor neurons left in the spinal cord of EphA4$^{+/-}$;SOD1$^{G93A}$ mice (n=9) compared to age-matched EphA4$^{+/+}$;SOD1$^{G93A}$ littermates (n=9). The protective effect of EphA4 depletion is most pronounced for large motor neurons (two-way ANOVA, $p_{genotype*motor\ neuron}$ size=0.031, Panel C). EphA4 depletion shows improved reinnervation of gastrocnemius neuromuscular junctions 20 days after sciatic nerve axotomy [27.40% reinnervation (EphA4$^{+/+}$, n=10) versus 44.87% (EphA4$^{+/-}$, n=8, OR 2.15+/−[1.76-2.63]), and 65.26% (EphA4$^{-/-}$, n=5, OR 4.98+/−[3.93-6.31], 200 neuromuscular junctions were scored for each mouse, Panel D).

To investigate whether the decreased EphA4 expression observed during disease progression in the SOD1G93A mouse (FIG. 10, Panels A-C) merely reflected the loss of motor neurons or the survival of motor neurons that expressed lower levels of EphA4, quantitative real-time PCR was performed for EphA4 of the cytoplasm of surviving motor neurons in the spinal cord of mutant SOD1 mice, obtained by laser capture microdissection. Remarkably, motor neurons still surviving in diseased SOD1$^{G93A}$ mice have lower EphA4 levels compared to pre-symptomatic SOD1$^{G93A}$ and control mice (FIG. 10, Panel D). Large motor neurons have been reported to be more vulnerable in ALS, while small motor neurons are resistant.[27-30] Further exploration was performed as to whether large motor neurons express higher levels of EphA4. Large motor neurons (>600 μm$^2$) were found to be more vulnerable in ALS as compared to smaller motor neurons (FIG. 11, Panel B). Moreover, qPCR of EphA4 in the cytoplasm of normal (nontransgenic) large and small motor neurons, obtained using LCM, showed that large motor neurons have higher expression levels of EphA4 (FIG. 11, Panel B). To corroborate this, the size of motor neurons in the ventral horn of the spinal cord of EphA4$^{+/-}$;SOD1$^{G93A}$ and EphA4$^{+/+}$;SOD1$^{G93A}$ mice was quantified and found that the protective effect of EphA4 knockdown is most pronounced on large motor neurons (FIG. 11, Panel C).

In mutant SOD1 mice, large motor neurons show early denervation and lack of axonal sprouting and compensatory reinnervation.[29,30] Therefore, the effect of EphA4 on sprouting and neuromuscular reinnervation capacity of spinal motor neurons after axotomy was evaluated. Interestingly, EphA4 dose-dependently inhibited neuromuscular reinnervation by motor axons after axotomy (FIG. 11, Panel D). These results show that EphA4 contributes to the differential vulnerability of motor neurons in ALS, and inhibits neuromuscular reinnervation by motor axons in denervating conditions. Thus, EphA4 may be an important factor in the early denervation of large motor neurons and late denervation of small motor neurons known to occur in ALS.

Example 4

Pharmacological Inhibition of EphA4 Attenuates Motor Neuron Degeneration In Vivo In order to explore whether exogenous intervention would yield similar results as genetic manipulation, EphA4 signaling in zebrafish and rat models was pharmacologically blocked for mutant SOD 1-induced motor neuron degeneration. For pharmacological inhibition, it was chosen to work with two compounds that block the EphA4 receptor that were previously described: 2,5-dimethylpyrrolyl benzoic acid (here called "C1"), which was identified in a small compound library screen, and a 12-amino-acid peptide (KYL peptide), identified in a phage library screen.[31-33]

Figure 12:
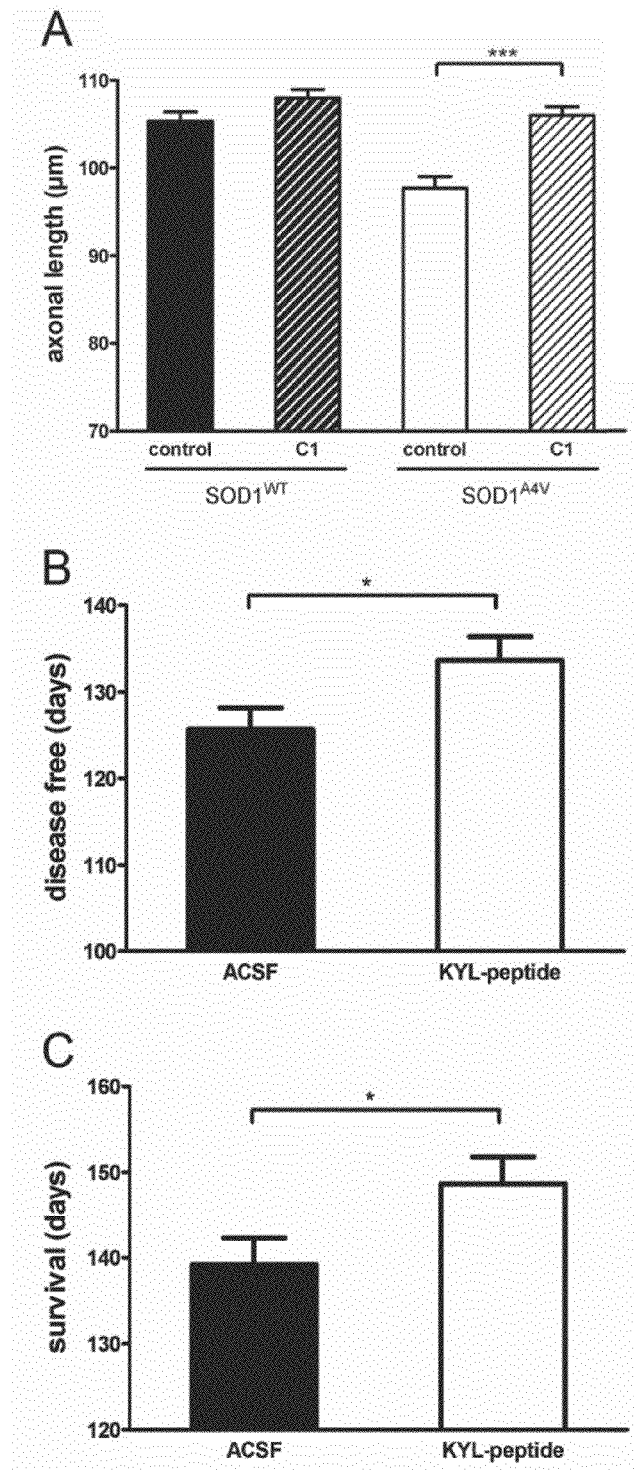
FIG. 12: Pharmacological inhibition of EphA4 receptor signaling protects against mutant SOD1 pathology in vivo. Effect of treatment with Compound 1 (C1, 500 μM) on the motor axon length of zebrafish embryos (30 hpf). DMSO (1/250 dilution) was used as control (Panel A). ANOVA and Bonferroni's multiple comparison tests were used for statistical analysis: SOD1$^{A4V}$/C1 (n=68) vs. SOD1$^{A4V}$/DMSO (n=76, p=3.54×10$^{-5}$). Effect of KYL-peptide (3 mM) treatment of 60-day-old SOD1$^{G93A}$ rats on disease onset (Panel B) and survival (Panel C). Artificial CSF (ACSF) was used as control. Average disease onset: 133 days (treated, n=21) versus 125 days (control, n=17, T-test p=0.044). Average survival: 148 days (treated, n=21) versus 139 days (controls, n=17, T-test p=0.041). Error bars are s.e.m.

No toxicity or pharmacokinetic data on C1 are available. Therefore, the highest dose was determined at which no general and motor axon toxicity was observed in the zebrafish when the compound was added to the water (Table 6). Treatment of SOD1$^{A4V}$ overexpressing zebrafish embryos with C1 was equally effective as morpholino-based RTK1 knockdown and completely rescued the mutant SOD1-induced axonopathy (FIG. 12, Panel A, and Table 4). To investigate the effect of EphA4 inhibition in higher vertebrates, SOD1$^{G93A}$ rats were treated with KYL peptide. This EphA4-blocking peptide, as well as other EphA4 inhibitors, were previously used in models of spinal cord injury and enhance recovery and axonal sprouting.[21,33,34] Therefore, the SOD1$^{G93A}$ rat, an established model for ALS, was treated with intracerebroventricular administration of this KYL peptide. This EphA4 antagonist delayed disease onset as measured by rotarod performance and prolonged survival in the SOD1$^{G93A}$ rat (FIG. 12, Panels B, C). Thus, while heterozygous deletion of EphA4 in SOD1$^{G93A}$ mice affected disease duration but not onset, pharmacological inhibition of EphA4 in SOD 1$^{G93A}$ rats delayed disease onset. This discrepancy may reflect differences between these two animal models or the difference between the two strategies used (deleting EphA4 expression from embryonic stages on, versus pharmacological inhibition in adult life). Furthermore, it may also be explained by the operational definition of "disease onset."

Example 5

EphA4 Modifies Disease Phenotype in Humans

In a large genetic association study on 2,925 ALS patients and 9,605 controls, no association was found between any of the 654 SNPs located in a 900 kb region surrounding the EPHA4 locus, and ALS susceptibility (none reached p<0.001). For analysis of survival in the disease only group (1,982 patients), none of 566 SNPs reached p<0.001. Association with age at onset in 2,892 patients showed that none of 569 SNPs reached p<0.01. To investigate whether expression levels of EPHA4 may affect disease parameters such as onset or survival in humans, EPHA4 expression was investigated in ALS patients and controls using quantitative real-time PCR on mRNA extracted from total blood. As predicted by the fish and rodent experiments, lower EPHA4 expression was strongly correlated with later onset of disease (n=158; p=4.63×10$^{-8}$, FIG. 13, Panel A), while no correlation was found between EPHA4 levels and age in controls (n=58, p=0.36). Then, an investigation was performed as to whether reduced EPHA4 expression similarly affected survival or disease duration. As expected, age at onset was a strong predictor of survival (p=4.7×10$^{-4}$). Interestingly, a multiple regression analysis including age at onset as a prognostic factor, revealed that disease duration again inversely correlated with EPHA4 expression (p=0.0378), demonstrating that the protective effect of low EPHA4 expression affected both age at onset and disease progression.

Figure 13:
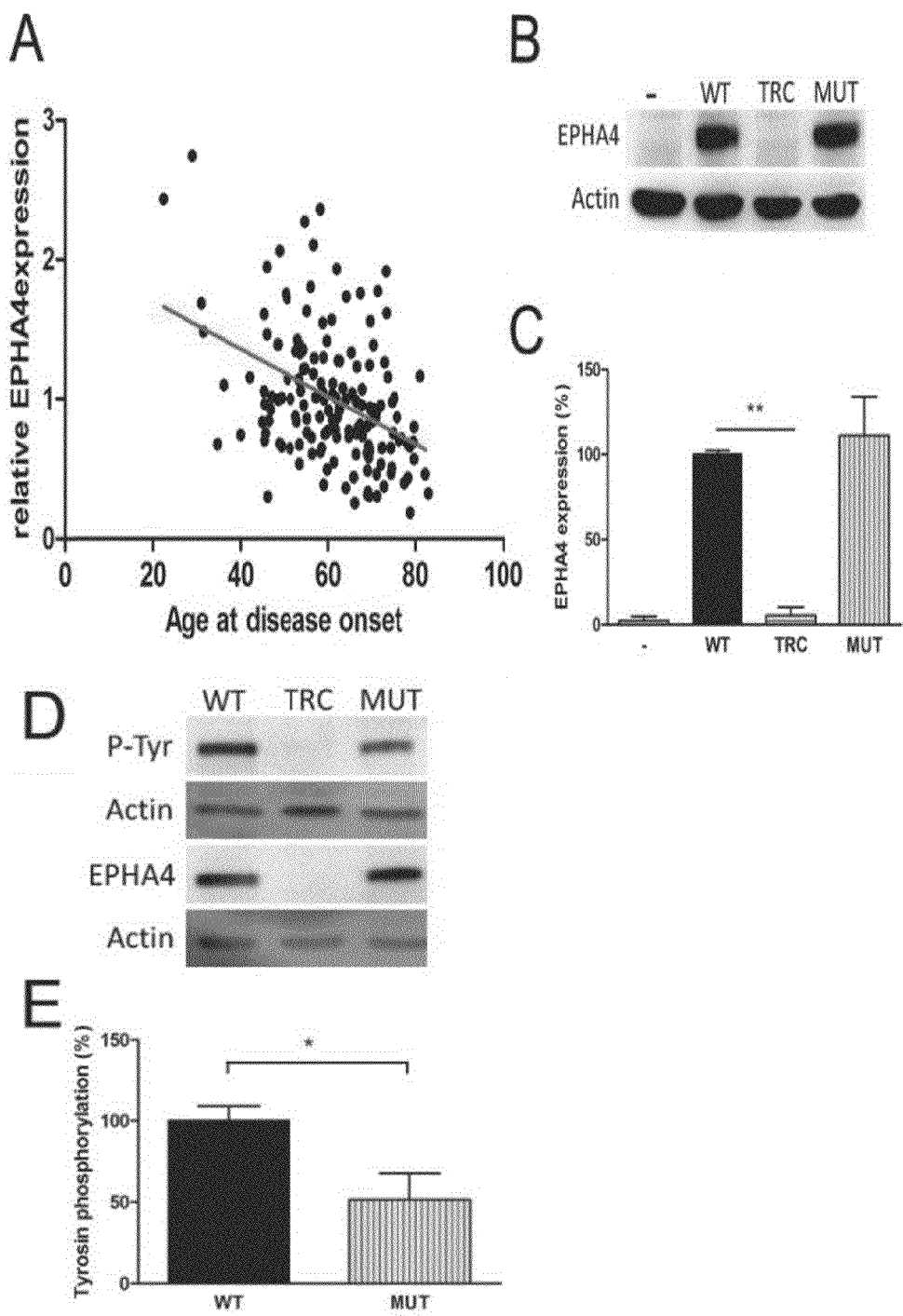
FIG. 13: EphA4 attenuates disease progression in human ALS patients. Quantitative PCR on mRNA extracted from total blood of 158 Dutch ALS cases. Y-axis shows relative EPHA4 expression, the X-axis shows age at disease onset. Linear regression p=4.63×10$^{-8}$, R$^2$=0.18 (Panel A). Western blot shows percentage EPHA4 expression in non-transfected (−), wild-type EPHA4 (WT), EPHA4 with nonsense mutation, R514X (TRC) and EPHA4 with missense mutation, R571Q (MUT) transfected NSC-43 cells (Panel B). While a truncation at amino acid 514 completely abolishes EPHA4 expression, EPHA4 levels are not affected by the mutation (Kruskal-Wallis, p=4.40×10$^{-4}$, n=7, Panel C). The R571Q mutation affects tyrosine phosphorylation of EPHA4, t-test, 0.029, n=4 (Panels D, E). Actin was used as loading control.

To further investigate the effect of EPHA4 on survival, direct sequencing of EPHA4 was performed in 96 familial and 96 sporadic ALS patients and identified 21 different variants (Table 7). Two of these affected highly conserved base pairs in the coding region of EPHA4. The two novel coding variants (E7:97, C>T, R514X and E8:112, G>A, R571Q) were found in a heterozygous state in two patients affected with ALS who had an unexpectedly long survival. R514X was identified in a patient who developed sporadic ALS at the age of 56 years and survived 89 months after symptom onset. R571Q was detected in a patient with familial ALS, diagnosed at the age of 43 years and still alive 149 months after onset. DNA samples from affected relatives of this familial case bearing the R571Q mutation were not available. Thus, both EPHA4 variants were associated with unusual long survival. The probability of these survivals is 0.082 (n=1237) for sporadic and 0.022 (n=627) for familial ALS. The mutant EPHA4$^{R514X}$ gene was predicted to generate a truncated protein lacking the final 472 amino acids that will be degraded by the cell, while the EPHA4$^{R571Q}$ gene mutation results in both a size and a charge change (from positive to neutral) and was predicted to impair function of the receptor (PMut software on the Internet at mmb2.pcb.ub.es:8080/PMut/). NSC43 cells were transfected with constructs encoding wild-type EPHA4, EPHA4$^{R514X}$ and EPHA4$^{R571Q}$. As predicted in silico, Western blot of cells transfected with the EPHA4 containing the nonsense mutation did not yield EphA4 expression (FIG. 13, Panels B, C). Transfecting NSC43 cells with EPHA4$^{R571Q}$ resulted in full-length protein expression; however, the EPHA4$^{R571Q}$ protein was affected in its signaling characteristics, as it showed strongly reduced tyrosine autophosphorylation, as was predicted in silico (FIG. 13, Panels D, E). These results show that, as suggested by the results obtained in fish, mice and rats, reduced EphA4 expression or signaling in humans is associated with attenuation of severity of disease phenotype.

Example 6

EphA4 Inhibition Protects Against TDP-43 Induced Motor Axonopathy

Figure 14:
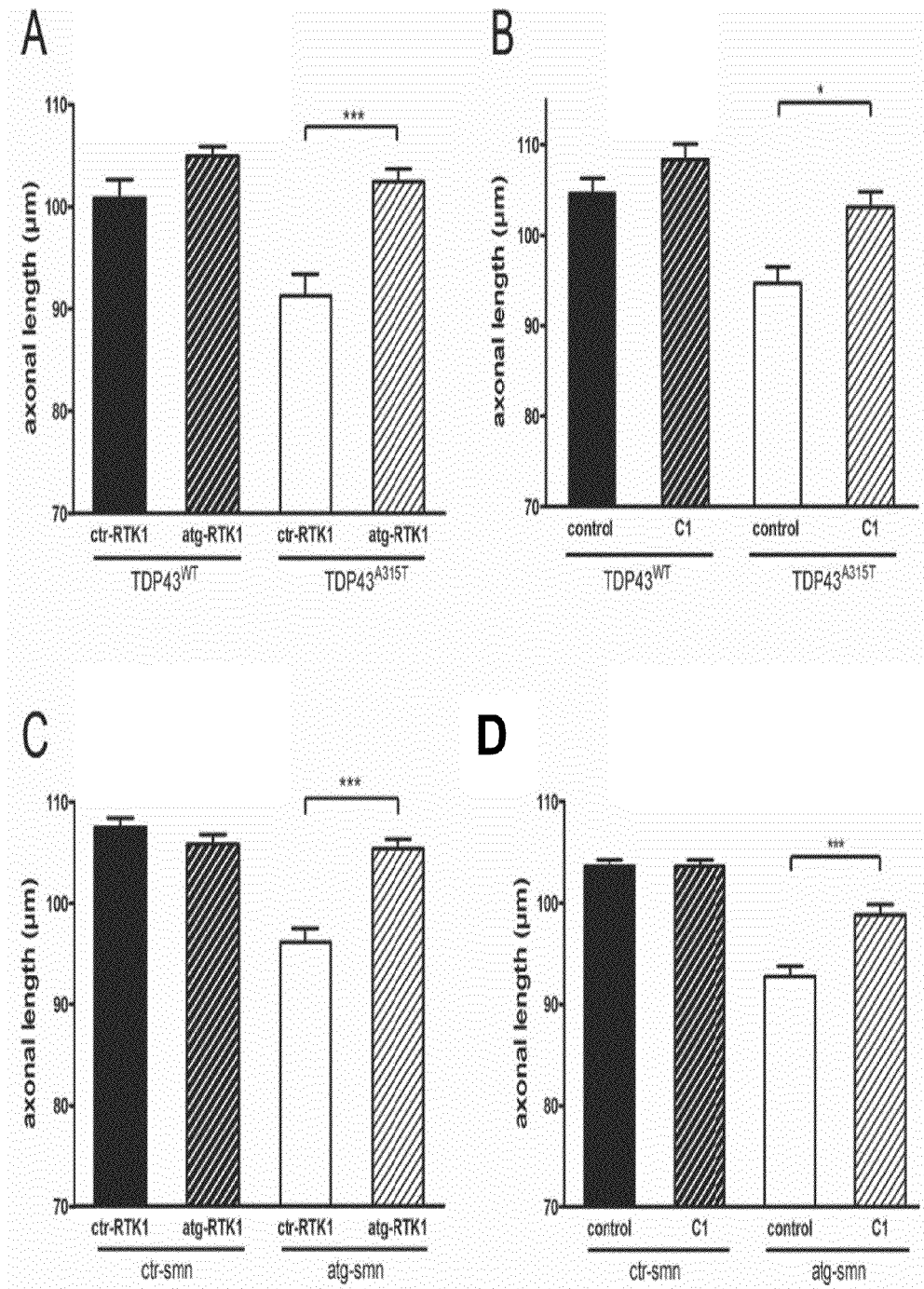
FIG. 14: Inhibiting EphA4 signaling rescues motor axonopathies induced by overexpression of mutant TDP-43 and knockdown of Smn. Y-axes show motor axon length of zebrafish embryos (30 hpf) expressing TDP$^{WT}$ (black bar) or TDP$^{A315T}$ (white bar) (Panels A, B) or with unaltered (black bar) or reduced expression levels of Smn (white bar) (Panels C, D). Smn knockdown was established by injection of 3 ng (Panel C) or 6 ng (Panel D) atg-smn morpholino. Ctr-smn morpholino was injected as control. RTK1 signaling was inhibited by injection of 3 ng atg-RTK1 morpholino (shaded bars) (Panels A, C) or by treatment with C1 (500 μM, shaded bars) (Panels B, D). Injection of ctr-RTK1 morpholino and application of a 1/250 dilution of DMSO were used as control. ANOVA and Bonferroni's multiple comparison tests were used for statistical analysis: TDP$^{A315T}$/atg-RTK1 (n=24) vs. TDP$^{A315T}$/ctr-RTK1 (n=34, p=7.86×10$^{-5}$, Panel A), TDP$^{A315T}$/C1 (n=21) vs. TDP$^{A315T}$/DMSO (n=21, p=0.045, Panel B), atg-smn/atg-RTK1 (n=35) vs. atg-smn/ctr-RTK1 (n=35, p=4.93×10$^{-8}$, Panel C), atg-smn/C1 (n=91) vs. atg-smn/DMSO (n=105, p=1.27×10$^{-6}$, Panel D). Error bars are s.e.m.

Mutations in SOD1 are the cause of familial ALS in only 20% of patients. Mutations in TARDBP, the gene encoding TDP-43, are estimated to be an even less frequent cause of familial ALS, but the interest in the role of TDP-43 in motor neuron degeneration is large because mislocation and aggregation, abnormal cleavage and hyperphosphorylation of this protein are found in sporadic ALS.[35] Therefore, the effect of EphA4 inhibition on the TDP-43-induced motor axonopathy in zebrafish embryos was investigated. Both knockdown of EphA4 (using the atg-RTK1 morpholino) and pharmacologically blocking EphA4 signaling (using CO rescued the outgrowth deficit and aberrant branching induced by mutant TDP-43 (FIG. 14, Panels A, B, and Table 8).

Example 7

EphA4 Inhibition Attenuates Motor Neuron Abnormalities in a Model for Spinomuscular Atrophy (SMA)

Figure 15:
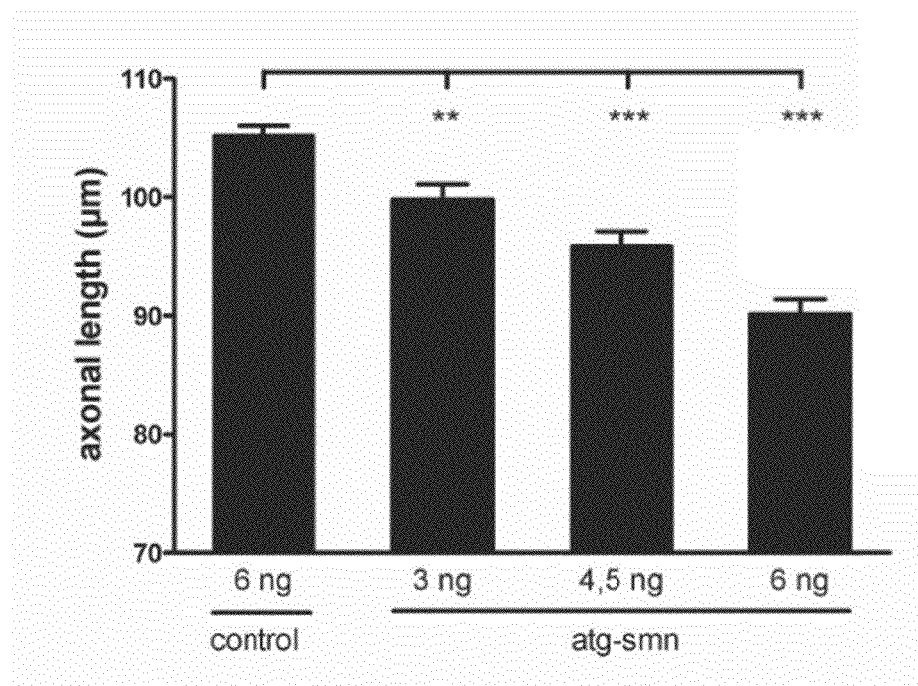
FIG. 15: Smn knockdown reduces the motor axon length in zebrafish embryos. Y-axis shows motor axon length of zebrafish embryos (30 hpf), injected with increasing amount of atg-smn morpholino. The non-functional five-base pair-mismatch control morpholino (ctr-smn) was used as control. ANOVA and Bonferroni's multiple comparison tests were used for statistical analysis: ctr-smn (6 ng, n=42) vs. 3 ng atg-smn (n=28, p=8.99×10$^{-3}$), 4.5 ng atg-smn (n=30, 3.37× 10$^{-7}$), 6 ng atg-smn (n=41, p<1×10-20). Error bars are s.e.m.

The hazardous role of an axonal repellent system such as the ephrin family may be involved in the failure of axonal maintenance in motor neuron disorders other than ALS as well. Therefore, it was investigated as to whether the protective effect obtained through inhibition of EphA4 was also found in a model of another motor neuron disease, spinomuscular atrophy (SMA). SMA is a frequently occurring lower motor neuron disorder characterized by muscle atrophy and weakness, with loss of reflexes. It is a severe disorder of infants and young children, but onset in early adulthood is possible. It is caused by loss of function mutations in SMN1, encoding Smn protein (survival of motor neuron). Less severe phenotypes are explained by the presence of SMN2 genes that give rise to limited amounts of functional Smn. As previously described,[15] knockdown of Smn in zebrafish embryos causes defects in motor axon outgrowth, a well-established model to study SMA (FIG. 15 and Table 9). Both EphA4 knockdown (using the RTK1 morpholino) and pharmacological inhibition of the EphA4 signaling (using C1) rescued the motor axon phenotype induced by knockdown of Smn (FIG. 14, Panels C, D, and Table 10). These observations suggest that the protective effect of blocking the axon repellent ephrin system may be generic to motor neuron and axonal degeneration.

Discussion

Small animal models for neurodegenerative disorders have been generated to perform compound screening and to identify disease-modifying genes. Previously, a zebrafish model was developed for ALS, characterized by a mutant SOD1-induced axonopathy.[13] Screening of this zebrafish model in the present study identifies EphA4 as a genetic factor that modifies the mutant SOD1 phenotype. Particularly, EphA4 knockdown rescues the mutant SOD1-induced axonopathy, in a dose-dependent manner, without affecting the motor axons in non-pathological conditions. Genetic deletion of EphA4 and pharmacological inhibition of EphA4 signaling attenuates motor neuron degeneration in a mouse and rat model for ALS. Most interestingly, it was found that reduced EphA4 expression in human patients correlates with reduced disease severity, demonstrating that genetic screening in zebrafish may identify disease modifiers for ALS in humans. Therefore, the study shows the validity of small animal models, such as zebrafish, to identify genetic factors that modify disease phenotype in ALS patients, and maybe in other types of motor neuron degeneration.

In addition, although in the mutant SOD1 mouse model axonal transport is disturbed as early as the first postnatal week in vivo, and even already during early embryonic development in vitro, the relevance of modeling a late age-onset neurodegenerative disease such as ALS in the developing zebrafish had been uncertain so far. The current study shows that these early models indeed yield results that are of relevance for late-onset diseases.

EPHA4 has previously not been identified as a disease modifier gene in genome-wide association studies in ALS. No association of ALS with SNPs was found in the EPHA4 gene, in spite of sufficient power based on the large sample size. The EPHA4 sequence variations in the coding regions identified in the present study are rare and escape genome-wide association studies.

Expression levels of EPHA4 were found to inversely correlate with disease onset and duration. Blood gene expression profiles have been successfully used to study CNS diseases such as Alzheimer's disease, Huntington's disease, bipolar disorder and schizophrenia.[36-41] It has been used in ALS as well.[42] It has recently been shown that, in spite of the tissue-specific regulation of a subset of genes, the majority of them show similar genetic variation in various organs.[43] Expression levels are likely to be regulated by a multiple of factors, which explain why this gene was not identified as a disease modifier in SNP-based approaches. This demonstrates that small animal screening yields results complementary to human genetic association studies.

Although axonal guidance factors have been hypothesized to play a role in neurodegenerative diseases,[44] evidence for the involvement of the ephrin system in neurodegeneration is limited. One study in *Drosophila* reported that the secreted MSP domain of VAPB interacts with the fly ephrin receptor. Mutations in VAPB, a very rare cause of familial ALS, precluded normal processing of this protein, which resulted in reduced MSP domain secretion. The same study identified EphA4 as a receptor for MSP in mammalian cells in vitro, and the blocking of this signaling pathway may contribute to pathology of ALS.[45] The results demonstrate EphA4 to be involved in the susceptibility of neurons to neurodegeneration, suggesting that development and neurodegeneration share common molecular pathways. Of interest is the finding that the protective effect of inhibition of the EphA4 receptor was independent of the cause of axonal degeneration but that the ephrin system may be a generic determinant of vulnerability of neurons to axonal degeneration.

The results show that EphA4 contributes to the differential vulnerability of motor neurons known to occur in ALS, and that this is reflected in limited axonal regeneration and neuromuscular reinnervation of motor neurons expressing high levels of this protein.

Although the effect on survival seems rather modest, the deletion of 50% of EphA4 in mice increases disease duration with more than 57%, which corresponds to an increase in survival in humans of 48 to 74 months, and reduced the slope of the loss of motor performance with about 50%. The long survival observed in the two patients by far exceeds what was found in rodent models. Therefore, indeed, based on the observations in these patients, the effect in humans may be larger than what is observed in mice. The most obvious explanation is that the high transgene expression in the SOD1$^{G93A}$ model results in a very aggressive disease, which may be less susceptible to modification, because of the overwhelming presence of the causative protein.

Furthermore, it was shown that pharmacological blockade of EphA4 using different compounds affects the disease, offering an interesting therapeutic avenue for preclinical research, for both the familial and the sporadic patients and even beyond the field of ALS on itself. These results also suggest that the toxicity of blocking EphA4 in the adult nervous system may be limited.

Thus, the ephrin system not only has a role as an axonal repellent system during development, but is also involved as a factor contributing to axonal retraction in the process of neurodegeneration in the adult organism.

Tables

TABLE 1

Morpholino-based knockdown screening in zebrafish

| | Amount of morpholinos | |
|---|---|---|
| | Neuronally expressed genes | Randomly chosen genes |
| Morphological defects | 6 | 67 |
| Aggravation | 37 | 95 |
| Rescue | 15 | 83 |
| Rescue >75% | 3 | 10 |

Effect of morpholino injection on the morphology and the motor axonal phenotype of SOD1$^{A4V}$ zebrafish embryos

TABLE 2

RTK2 knockdown reduces the percentage of affected mutant SOD1-overexpressing fish.

| | | ctr-RTK2 | atg-RTK2 | | |
|---|---|---|---|---|---|
| | | 4.5 ng % (n) | 1.5 ng % (n) | 3.0 ng % (n) | 4.5 ng % (n) |
| wtSOD1 | | 16 (158) | — | — | 12 (123) |
| mtSOD1 | A4V | 33 (39) | 29 (41) | 18 (44) | 8* (37) |
| | G93A | 66 (53) | 55 (47) | 50 (54) | 23° (56) |
| | G37R | 47 (38) | 34 (26) | 8 (25) | 16# (36) |

Effect of RTK2 knockdown (established by injection of atg-RTK2 morpholino) on the percentage of affected wild-type SOD1 or mutant SOD1 (A4V, G93A, G37R) zebrafish embryos (30 hpf). Ctr-RTK2 morpholino was used as control. An embryo was considered as affected when it had more than 10% abnormally branched motor axons. Significance of mtSOD1/ctr-RTK2 (4.5 ng) vs. mtSOD1/atg-RTK2 (4.5 ng) was determined by Mann-Whitney test, * p=0.0075, ° p=0.039 and # p=0.0052.

TABLE 3

RTK2 knockdown reduces the percentage of affected SOD1A4V embryos.

| | ctr-RTK2 | spl-RTK2 | | |
|---|---|---|---|---|
| | 1.5 ng % (n) | 0.4 ng % (n) | 0.8 ng % (n) | 1.5 ng % (n) |
| SOD1WT | 2 (41) | — | — | — |
| SOD1A4V | 46 (28) | 40 (30) | 19 (31) | 13* (31) |

Significance of SOD1A4V/ctr-RTK2 (1.5 ng) vs. SOD1A4V/spl-RTK2 (1.5 ng) was determined by Mann-Whitney test, *p=0.005.

TABLE 4

Knockdown and pharmacological inhibition of RTK1 reduces the percentage of affected mutant SOD1-overexpressing fish.

| | ctr-RTK1 4.5 ng % (n) | atg-RTK1 1.5 ng % (n) | 3 ng % (n) | 4.5 ng % (n) | control % (n) | C1 500 μM % (n) |
|---|---|---|---|---|---|---|
| SOD1$^{WT}$ | 13 (40) | — | — | 14 (14) | 12 (32) | 15 (32) |
| SOD1$^{A4V}$ | 42 (24) | 38 (24) | 22 (33) | 8* (26) | 38 (40) | 11° (26) |

Mann-Whitney test was used to determine significance between SOD1A4V/ctr-RTK1 (4.5 ng) vs. SOD1A4V/atg-RTK1 (4.5 ng, * p=0.0056) and between SOD1A4V/control vs. SOD1A4V/C1 (° p=0.017). 1/250 dilution of DMSO was applied as control.

TABLE 5

Non-mendelian distribution of EphA4−/− mice

| | Observed (%) | Expected (%) | N |
|---|---|---|---|
| EphA4+/+ | 38.10 | 25 | 269 |
| EphA4+/− | 56.65 | 50 | 400 |
| EphA4−/− | 5.24 | 25 | 37 |

Cross-breeding heterozygous EphA4 males with heterozygous EphA4 females produced a pronounced lower number of EphA4 knockout mice as should be expected according to Mendelian inheritance.

TABLE 6

Toxicity analysis of Compound 1.

| C1 (μM) | death | malformed | normal |
|---|---|---|---|
| 0 | 5.82 | 1.94 | 92.23 |
| 250 | 6.12 | 5.10 | 88.77 |
| 500 | 2.80 | 3.74 | 93.45 |
| 750 | 11.2 | 12.93 | 75.86 |
| 1000 | 20 | 80 | 0 |

Different concentrations of C1 were dissolved in the water of 6 hpf-old zebrafish embryos. At 30 hpf, toxicity (%) of C1 was investigated by analyzing total body shape of the embryos.

TABLE 7

EPHA4 gene mutational analysis in familial and sporadic ALS.

| Variant | Type of variant | Geno-type | Frequency (%) FALS | Frequency (%) SALS |
|---|---|---|---|---|
| Rs17299591 | intronic | GG | 90 | 96.2 |
| | | GT | 9.8 | 38 |
| | | TT | 0 | 0 |
| Rs2288627 | intronic | CC | 8.8 | 11.1 |
| | | CT | 36.2 | 35.8 |
| | | TT | 54.9 | 53 |
| Rs2288628 | intronic | CC | 98.8 | 97.8 |
| | | CA | 0 | 0 |
| | | AA | 1.2 | 2.2 |
| Rs2303897 | intronic | GG | 97.5 | 93.1 |
| | | GA | 0 | 0 |
| | | AA | 2.5 | 6.9 |
| Rs41272711 | intronic | CC | 97.6 | 97.7 |
| | | CG | 2.4 | 2.3 |
| | | GG | 0 | 0 |
| Rs3213844 | intronic | AA | 14.1 | 11.6 |
| | | AG | 34.1 | 34.9 |
| | | GG | 51.8 | 53.5 |
| Rs10498111 | coding-synonymous (K625K) | AA | 100 | 98.9 |
| | | AG | 0 | 1.1 |
| | | GG | 0 | 0 |
| Rs56159060 | coding-synonymous (R769R) | CC | 100 | 98.8 |
| | | CA | 0 | 0 |
| | | AA | 0 | 1.2 |
| Rs35860178 | coding-synonymous (T060T) | GG | 80.5 | 77.9 |
| | | GA | 17.2 | 20.9 |
| | | AA | 2.3 | 1.2 |
| Novel (I1: +135) | intronic | GG | 99 | 100 |
| | | GT | 1 | 0 |
| Novel (I5: +37) | intronic | GG | 99 | 100 |
| | | GA | 1 | 0 |
| Novel (I8: +30) | intronic | CC | 100 | 99 |
| | | CT | 0 | 1 |
| Novel (I9: +119) | intronic | CC | 99 | 100 |
| | | CA | 1 | 0 |
| Novel (I13: +20) | intronic | TT | 97.9 | 100 |
| | | TA | 2.1 | 0 |
| Novel (I13: +13) | intronic | GG | 100 | 99 |
| | | GC | 0 | 1 |
| Novel (I14: −13) | intronic | CC | 100 | 96.9 |
| | | CT | 0 | 3.1 |
| Novel (I16: +23) | intronic | CC | 100 | 99 |
| | | CT | 0 | 1 |
| Novel (E10: 32) | coding-synonymous (T602T) | CC | 100 | 99 |
| | | CT | 0 | 1 |
| Novel (chr2: 221, 992, 861) | 3'UTR | TT | 99 | 99 |
| | | TA | 1 | 1 |
| Novel (E7: 97) | coding-nonsense (R514X)[1] | CC | 100 | 99 |
| | | CT | 0 | 1 |
| Novel (E8: 112) | coding-nonsynonymous (R571Q)[2] | GG | 99 | 100 |
| | | GA | 1 | 0 |

Direct sequencing of the EPHA4 gene in 96 familial and 96 sporadic ALS patients identified 21 variants of which 9 were known and 12 were novel. The very well-conserved variants (1-2) were analyzed for prevalence in controls using TaqMan assays. Frequency in controls: CT: 0%, n=1100[1] and AG: 0%, n=1100[2].

TABLE 8

Knockdown and pharmacological inhibition of RTK1 reduces the percentage affected TDP43A315T embryos.

| | ctr-RTK1 % (n) | atg-RTK1 % (n) | control % (n) | C1 % (n) |
|---|---|---|---|---|
| TDP$^{WT}$ | 18 (43) | 9 (42) | 29 (48) | 33 (36) |
| TDP$^{A315T}$ | 36 (36) | 11* (43) | 62 (21) | 25° (16) |

Mann-Whitney test was used to determine significance between TDPA315T/ctr-RTK1 (4.5 ng) vs. TDPA315T/atg-RTK1 (4.5 ng, * p=0.001) and between TDPA315T/control vs. TDPA315T/C1 (° p=0.029). Control=1/250 DMSO and C1=500 µM.

TABLE 9

Morpholino-based smn knockdown induces abnormally branched and truncated motor axons.

| | ng | branching affected (%) | truncation affected (%) | n |
|---|---|---|---|---|
| ctr-smn | 6 | 14 | 0 | 36 |
| atg-smn | 3 | 39 | 7 | 28 |
| | 4.5 | 46 | 11 | 28 |
| | 6 | 71* | 42° | 38 |

Effect of smn knockdown, induced by injection of increasing amounts of atg-smn morpholino, on the percentage affected embryos. An embryo was considered as affected when it had more than 10% abnormally branched or more than 5% truncated motor axons. Significance of ctr-smn (6 ng) vs. atg-smn (6 ng) was determined by Mann-Whitney test, *p=3×10-4, ° p=1.3×10-4.

Materials and Methods

Animals

Adult zebrafish (AB strain) and embryos, EphA4−/− mice (C57BL/6 background), mice overexpressing human SOD1WT/G93A (C57BL/6 background) and rats overexpressing human SOD 1G93A (Holtzman background) were maintained in accordance with the Guide of Care and Use of Experimental Animals of the ethical committee of the Katholieke Universiteit Leuven.

Morpholino Screening in Zebrafish

A morpholino database of translation-blocking morpholinos (atg-mo) was used to perform a morpholino-based knockdown screening in a zebrafish model for ALS.[13] The standard control morpholino (5'-CCTCTTACCTCAGTTACAATT-TATA-'3) (SEQ ID NO:4), provided by Gene tools, was used as control. Three nanograms of morpholino were co-injected with 1.43 ng of SOD1 mRNA and the effect of gene knockdown on the mutant SOD1-induced axonopathy analyzed. Each morpholino was tested in two separate experiments. Only morphologically normal embryos were included for further analysis. Overexpression of SOD1 or TDP-43, applied to validate the protective morpholino, was established by injection of 1.76 ng SOD1 mRNA or 1.43 ng TDP-43 mRNA, respectively. Antisense morpholinos to knockdown zebrafish RTK1, RTK2, Smn and their five base pair-mismatch control morpholinos were developed by Gene tools: atg-RTK1 (5'-CTGTGAACACAAGCGCAGCCATTGG-'3) (SEQ ID NO:5), atg-RTK2 (5'-AATCCAAAGGGTAGCCA-TTTTCAGG-'3) (SEQ ID NO:6), splice-RTK2 (5'-CCTC-CCACTGA-AAATGGACAGAGGA-'3) (SEQ ID NO:7) and atg-smn (5'-CGACATCTTCTGCACCATTGGC-3') (SEQ ID NO:8). Compound 1 (2,5-dimethylpyrrolyl benzoic acid, Matrix Scientific) dissolved in DMSO was added to the water of 6-hpf-old zebrafish embryos.

Evaluation of Mice and Rats

EphA4−/− mice were mated with SOD1G93A mice for at least six generations. All experiments were littermate and gender controlled. An accelerating rotarod treadmill (Ugo Basile), rotating from 4 rpm to 40 rpm for 300 seconds was used to evaluate motor performance. Each mouse was given three trials of 300 seconds, three times a week started at eight weeks after birth. Disease onset was defined as the time point when best rotarod performance was reduced with more than 50%. When mice could no longer roll over within 20 seconds after being placed on their back, they were sacrificed and this time point was considered as the time of death. The EphA4 blocking peptide (KYLPYWPVLSSL (SEQ ID NO:1)-95% purity; Eurogentec) was a 3 mM solution in artificial cerebrospinal fluid and infused into the left lateral ventricle of 60-day-old female rats, using mini-osmotic pumps (28 days, 0.25 μl/h, Model 2004, Alzet) as previously described.[46] Disease onset, progression and survival of SOD1G93A rats were analyzed by weight and rotarod performance (five times for three minutes at 15 rpm) three times a week. Disease onset was defined when the rats failed to run three times, three minutes on the rotarod. When rats could no longer lift themselves, which was considered as end stage, they were euthanized.

Sciatic Nerve Axotomy

After anesthesia with 3% isofluorane, a small incision was made in the upper tight, at midtight level, unilateral, and muscles were separated in order to visualize the sciatic nerve. The nerve was then transsected. Afterward, muscle and skin were sutured separately.

Muscle, Ventral Horn and Sciatic Nerve Analysis

Disease onset and late-symptomatic stages were considered as the time point when mice could not sustain the hanging wire test for more than 60 seconds and 2 seconds, respectively. When age-matched, all littermates were sacrificed when at least one mouse did not succeed the hanging wire test to define disease stage. When disease-matched, mice were sacrificed when they failed the hanging wire test; hence, littermates may have been sacrificed at different time points. Gastrocnemic muscles were snap frozen in isopentane, which was cooled by immersion in liquid nitrogen. Cryostat sections (20 μm) were stained with hematoxylin and eosin (H&E), modified Gomori trichrome and nicotinamide adenosine dinucleotide (NADH)-tetrazolium reductase. Longitudinal cryostat sections (40 μm) were immunostained with NF-200 (1/200; Sigma), and Alexa-488 conjugated α-bungarotoxin to visualize the neuromuscular junctions (1/500; Invitrogen). Sciatic nerves were dissected, fixed in 2.5% glutaraldehyde, colored with osmium tetroxide, dehydrated and embedded in epoxy resin. Spinal cords were dissected, fixed in 4% paraformaldehyde and dehydrated in 30% sucrose. Sections of 7 μm thickness were made of paraffin-embedded lumbar spinal cord, deparaffinated, and stained by H&E. Cryostat sections of 20 μm thickness were fresh frozen in tissue-tec (Sakura) and used for cresyl violet (Sigma) and immunostaining. Of every tenth slide and for 10 slides per animal, the area of normal-appearing neurons in the ventral horn of the lumbar spinal cord was calculated using Axiovision 4 software (Zeiss) and the number of neurons in different size groups determined. Neurons in the ventral horn of the lumbar spinal cord, with a cell body area >250 μm$^2$, were considered motor neurons. Cresyl violet-stained motor neurons, located in the ventral horn of the lumbar spinal cord, were dissected using a laser capture microscope (Zeiss) by using membrane slides 1.0 PEN and Adhesive Cap 500 opaque (Zeiss). To separate small and large motor neurons, only motor neurons of which their nucleus was visible were microdissected. Co-labeling was established by immunostaining for rabbit EphA4 (1/100, Upstate), mouse NeuN (1/200, Chemicon), mouse GFAP (1/500, Invitrogen), rabbit Iba1 (1/300, Wako), guinea pig GLT-1 (1/100, Millipore) and Alexa-488/555 labeled antibodies (1/500, Invitrogen).

EPHA4 Constructs and Cell Culture Treatments

The R514X and R571Q mutations were inserted in a human EPHA4 vector (Origene) using the QuikChange Site-Directed Mutagenesis Kit (Stratagene). The immortalized motor neuron cell line NSC-34 was cultured as previously described.[47] Constructs were transfected in NSC-43 cells using Lipofectamin reagent 2000 (Invitrogen). For phosphotyrosine blots, cells were stimulated for 30 minutes with 5 μg/ml ephrin-a5 (R&D), preclustered with 1 μg/ml human IgG (Jackson ImmunoResearch) before harvesting.

Western Blot

Mice spinal cord and 30 hpf old, dechorionated and deyolked zebrafish embryos, and NSC-43 cells were homogenized in buffer: 50 mM Triz/HCl, pH 7.5, 120 mM NaCl, 1% TRITON® X-100, 1 mM sodium orthovanadaat, 2 mM PMSF, complete protease inhibitor (Roche). Protein concentration was determined using the micro-BCA protein assay reaction kit 207 (Pierce). Equal amounts of protein were loaded on the same blot. For Western blot, precast 4-12% Bis-Tris gels (Invitrogen), rabbit SOD1 antibody (1/10000, Stressgen), mouse β-actin antibody (1/5000, Sigma-Aldrich), rabbit GLT-1 (1/1000, α-diagnostics), mouse EphA4 antibody (1/1000, Zymed) and mouse phosphotyrosine (1/1000, Invitrogen) were used. Because of the high similarity between zebrafish RTK1 and mouse EphA4, the mouse antibody was able to detect zebrafish RTK1. Horseradish peroxidase conjugated secondary antibodies (1/5000, Santa Cruz) and enhanced chemiluminescent (ECL) substrate (Pierce) were used to visualize the protein bands. Blots were scanned with the Image Quant LAS 4000.

Whole-Mount Immunohistochemistry

Zebrafish rhombomeres were whole-mount immunostained with rabbit EphA4 (1/100, Upstate) and zebrafish ephrin-b2 (1/200, R&D) primary antibodies and Alexa-488/555-labeled secondary antibodies.

RT-PCR

Total RNA was extracted from zebrafish embryos, using the TRIPURE® method.[13] RNA was quantified and reverse-transcribed using random hexamer priming and mMLV. RTK2 was amplified by PCR by using forward primer: CGGAATTACCCAGAGAATGAAG (SEQ ID NO:9) and reverse primer: AAACTGTGTGGAGGACATTTGG (SEQ ID NO:10). The cycling reaction was 95° C. for 5 minutes, 34 cycles of 95° C. for 10 seconds, 57.5° C. for 15 seconds, 72° C. for 40 seconds, followed by 72° C. for 7 minutes.

Quantitative Real-Time PCR

Patients were recruited at the referral clinic for motor neuron disease at the University Medical Center Utrecht, The Netherlands, and RNA was extracted from peripheral whole blood using PaxGene® tubes and PaxGene® extraction kit (Qiagen). Quantitative real-time PCR expression data were obtained from total blood of 158 Dutch ALS patients, containing all blood cells including polymorphonuclear leukocytes, mononuclear cells, platelets and red blood cells. Total leukocyte counts and leukocyte differentiation showed no significant differences between included patients and controls. The Hs00177874_m1 assay against human EPHA4, the Hs99999905_m1 assay against human GAPDH (endogenous control, Applied Biosystems), the Mm01256005_m1 assay against mouse EphA4, the Mm00839502_m1 assay against mouse polr2a, TaqMan® universal PCR Master Mix (Applied Biosystems) and the 7900HT Fast Real-time PCR system (Applied Biosystems) were used.

Human Association Study for EPHA4

In total, 3,001 ALS patients and 9,676 controls from seven recruitment sites in six different countries (Belgium, The Netherlands, Sweden, Ireland, UK and US) were included in the study. Genotyping data for a total of 86 SNPs in the EPHA4 region genotyped with ILLUMINA® Hap300 or Hap550 platforms were available. Genotyping success rate per individual and per SNP was required to be >95%, resulting in a total of 2,925 cases and 9,605 controls and 82 SNPs in the analysis. No deviation from Hardy-Weinberg equilibrium was observed (all P>0.001). Each study population was imputed separately using Mach2 version 1.0.16 with a reference set of 770 SNPs from HapMap Phase 2 Release 22. All dosage files were combined and analyzed using the dosage option in Plink version 1.07 and using study population as a covariate. Quality of imputation was evaluated with the Plink information content (INFO) measure (required to be >0.8). For analysis of clinical variables, additional covariates (gender, site of onset, age at onset, recruitment site) were included.

Mutational Sequencing

DNA was isolated from venous blood of 96 sporadic and 96 familial ALS patients. Whole genome amplification was performed on the DNA samples using the ILLUSTRA GENOMI-PHI® V2 DNA Amplification kit (GE HealthCare). EPHA4 exons 1 through 17 and the 3' UTR of this gene were amplified by PCR with primers that were designed using Primer 3.0. AMPLITAQ® Gold PCR Master Mix 2500U (Applied Biosystems) was used to carry out a touchdown PCR: 95° C. for 5 minutes, 30 cycles at 95° C. for 30 seconds, 65° C. for 30 seconds; with a −0.5° C. decrement of temperature per cycle, and 72° C. for 1 minute. Additionally, 15 cycles at 95° C. for 30 seconds, 65° C. for 30 seconds, 72° C. for 1 minute and 7 minutes at 72° C. PCR products were analyzed on a 1.5% agarose gel and sequenced bidirectionally. Every novel nucleotide change was double-checked using purified DNA from the given patient in order to confirm that it was a real change. A high-throughput SNP genotyping was performed using TAQMAN® assay in a larger set of cases and controls.

Statistics

STATISTICA software was used for statistical analysis and the following tests were performed: T-test, one-way anova, log rank test, odds ratio, Mann-Whitney and Kruskal-Wallis test as specified in the main text and figure legends. Error bars are s.e.m. and reported values in the text indicate average+/−s.e.m. To analyze the rotarod data, slopes of their rotarod performance were constructed for all animals (from disease onset [50% of maximum rotarod performance] until complete rotarod failure [0% of maximum rotarod performance]) and used t-test to compare the slopes between the groups. A simple regression model was applied to define the correlation between age at disease onset and EPHA4 expression (two-tailed). A multiple regression model, including EPHA4 expression and disease duration as variables, was applied to reveal a correlation for disease duration in the same direction as for age at onset (regression coefficient=−0.16, one-tailed).

References

1. Rosen, D. R., et al. Mutations in Cu/Zn superoxide dismutase gene are associated with familial amyotrophic lateral sclerosis. *Nature* 362, 59-62 (1993).
2. Sreedharan, J., et al. TDP-43 mutations in familial and sporadic amyotrophic lateral sclerosis. *Science* 319, 1668-1672 (2008).
3. Kwiatkowski, T. J., Jr., et al. Mutations in the FUS/TLS gene on chromosome 16 cause familial amyotrophic lateral sclerosis. *Science* 323, 1205-1208 (2009).
4. Gitcho, M. A., et al. TDP-43 A315T mutation in familial motor neuron disease. *Ann. Neurol.* 63, 535-538 (2008).
5. Vance, C., et al. Mutations in FUS, an RNA processing protein, cause familial amyotrophic lateral sclerosis type 6. *Science* 323, 1208-1211 (2009).
6. Penco, S., et al. Phenotypic Heterogeneity in a SOD1G93D Italian ALS Family: An Example of Human Model to Study a Complex Disease. *J. Mol. Neurosci.*
7. Kim, W., et al. Anticipation and phenotypic heterogeneity in Korean familial amyotrophic lateral sclerosis with superoxide dismutase 1 gene mutation. *J. Clin. Neurol.* 3, 38-44 (2007).
8. Fogh, I., et al. Age at onset in sod1-mediated amyotrophic lateral sclerosis shows familiality. *Neurogenetics* 8, 235-236 (2007).
9. White, R. M., et al. DHODH modulates transcriptional elongation in the neural crest and melanoma. *Nature* 471, 518-522.
10. Gwack, Y., et al. A genome-wide *Drosophila* RNAi screen identifies DYRK-family kinases as regulators of NFAT. *Nature* 441, 646-650 (2006).
11. Hao, L., et al. *Drosophila* RNAi screen identifies host genes important for influenza virus replication. *Nature* 454, 890-893 (2008).
12. Rohde, C. B., F. Zeng, R. Gonzalez-Rubio, M. Angel, and M. F. Yanik. Microfluidic system for on-chip high-throughput whole-animal sorting and screening at subcellular resolution. *Proc. Natl. Acad. Sci. U.S.A.* 104, 13891-13895 (2007).
13. Lemmens, R., et al. Overexpression of mutant superoxide dismutase 1 causes a motor axonopathy in the zebrafish. *Hum. Mol. Genet.* 16, 2359-2365 (2007).
14. Laird, A. S., et al. Progranulin is neurotrophic in vivo and protects against a mutant TDP-43-induced axonopathy. *PLoS One* 5, e13368.
15. McWhorter, M. L., U. R. Monani, A. H. Burghes, and C. E. Beattie. Knockdown of the survival motor neuron (Smn) protein in zebrafish causes defects in motor axon outgrowth and pathfinding. *J. Cell Biol.* 162, 919-931 (2003).
16. Cooke, J. E., H. A. Kemp, and C. B. Moens. EphA4 is required for cell adhesion and rhombomere-boundary formation in the zebrafish. *Curr. Biol.* 15, 536-542 (2005).
17. Xu, Q., G. Alldus, H. Holder, and D. G. Wilkinson. Expression of truncated Sek-1 receptor tyrosine kinase disrupts the segmental restriction of gene expression in the *Xenopus* and zebrafish hindbrain. *Development* 121, 4005-4016 (1995).
18. Klein, R. Bidirectional modulation of synaptic functions by Eph/ephrin signaling. *Nat. Neurosci.* 12, 15-20 (2009).
19. Kullander, K., et al. Role of EphA4 and EphrinB3 in local neuronal circuits that control walking. *Science* 299, 1889-1892 (2003).
20. Dottori, M., et al. EphA4 (Sek1) receptor tyrosine kinase is required for the development of the corticospinal tract. *Proc. Natl. Acad. Sci. U.S.A.* 95, 13248-13253 (1998).
21. Goldshmit, Y., M. P. Galea, G. Wise, P. F. Bartlett, and A. M. Turnley. Axonal regeneration and lack of astrocytic gliosis in EphA4-deficient mice. *J. Neurosci.* 24, 10064-10073 (2004).
22. Filosa, A., et al. Neuron-glia communication via EphA4/ephrin-A3 modulates LTP through glial glutamate transport. *Nat. Neurosci.* 12, 1285-1292 (2009).
23. Rothstein, J. D., L. J. Martin, and R. W. Kuncl. Decreased glutamate transport by the brain and spinal cord in amyotrophic lateral sclerosis. *N. Engl. J. Med.* 326, 1464-1468 (1992).
24. Rothstein, J. D., M. Van Kammen, A. I. Levey, L. J. Martin, and R. W. Kuncl. Selective loss of glial glutamate transporter GLT-1 in amyotrophic lateral sclerosis. *Ann. Neurol.* 38, 73-84 (1995).
25. Guo, H., et al. Increased expression of the glial glutamate transporter EAAT2 modulates excitotoxicity and delays 26. Rothstein, J. D., et al. Beta-lactam antibiotics offer neuroprotection by increasing glutamate transporter expression. *Nature* 433, 73-77 (2005).
27. Bakels, R. and D. Kernell. Matching between motoneurone and muscle unit properties in rat medial gastrocnemius. *J. Physiol.* 463, 307-324 (1993).
28. Gardiner, P. F. Physiological properties of motoneurons innervating different muscle unit types in rat gastrocnemius. *J. Neurophysiol.* 69, 1160-1170 (1993).
29. Frey, D., et al. Early and selective loss of neuromuscular synapse subtypes with low sprouting competence in motoneuron diseases. *J. Neurosci.* 20, 2534-2542 (2000).
30. Pun, S., A. F. Santos, S. Saxena, L. Xu, and P. Caroni. Selective vulnerability and pruning of phasic motoneuron axons in motoneuron disease alleviated by CNTF. *Nat. Neurosci.* 9, 408-419 (2006).
31. Noberini, R., et al. Small molecules can selectively inhibit ephrin binding to the EphA4 and EphA2 receptors. *J. Biol. Chem.* 283, 29461-29472 (2008).
32. Murai, K. K., et al. Targeting the EphA4 receptor in the nervous system with biologically active peptides. *Mol. Cell Neurosci.* 24, 1000-1011 (2003).
33. Goldshmit, Y., et al. EphA4 blockers promote axonal regeneration and functional recovery following spinal cord injury in mice. *PLoS One* 6, e24636 (2011).
34. Fabes, J., P. Anderson, C. Brennan, and S. Bolsover. Regeneration-enhancing effects of EphA4 blocking peptide following corticospinal tract injury in adult rat spinal cord. *Eur. J. Neurosci.* 26, 2496-2505 (2007).
35. Neumann, M., et al. Ubiquitinated TDP-43 in frontotemporal lobar degeneration and amyotrophic lateral sclerosis. *Science* 314, 130-133 (2006).
36. Macs, O. C., et al. Transcriptional profiling of Alzheimer blood mononuclear cells by microarray. *Neurobiol. Aging* 28, 1795-1809 (2007).
37. Borovecki, F., et al. Genome-wide expression profiling of human blood reveals biomarkers for Huntington's disease. *Proc. Natl. Acad. Sci. U.S.A.* 102, 11023-11028 (2005).
38. Gladkevich, A., H. F. Kauffman, and J. Korf. Lymphocytes as a neural probe: potential for studying psychiatric disorders. *Prog. Neuropsychopharmacol. Biol. Psychiatry* 28, 559-576 (2004).
39. Glatt, S. J., et al. Comparative gene expression analysis of blood and brain provides concurrent validation of SELENBP1 up-regulation in schizophrenia. *Proc. Natl. Acad. Sci. U.S.A.* 102, 15533-15538 (2005).
40. Matigian, N. A., et al. Fibroblast and lymphoblast gene expression profiles in schizophrenia: are non-neural cells informative? *PLoS One* 3, e2412 (2008).
41. Tsuang, M. T., et al. Assessing the validity of blood-based gene expression profiles for the classification of schizophrenia and bipolar disorder: a preliminary report. *Am. J. Med. Genet. B. Neuropsychiatr. Genet.* 133B, 1-5 (2005).
42. Saris, C. G., et al. Weighted gene co-expression network analysis of the peripheral blood from Amyotrophic Lateral Sclerosis patients. *BMC Genomics* 10, 405 (2009).
43. Fu, J., et al. Unraveling the regulatory mechanisms underlying tissue-dependent genetic variation of gene expression. *PLoS Genet* 8, e1002431 (2012).
44. Schmidt, E. R., R. J. Pasterkamp, and L. H. van den Berg. Axon guidance proteins: novel therapeutic targets for ALS? *Prog. Neurobiol.* 88, 286-301 (2009).
45. Tsuda, H., et al. The amyotrophic lateral sclerosis 8 protein VAPB is cleaved, secreted, and acts as a ligand for Eph receptors. *Cell* 133, 963-977 (2008).
46. Storkebaum, E., et al. Treatment of motoneuron degeneration by intracerebroventricular delivery of VEGF in a rat model of ALS. *Nat. Neurosci.* 8, 85-92 (2005).
47. Cashman, N. R., et al. Neuroblastoma×spinal cord (NSC) hybrid cell lines resemble developing motor neurons. *Dev. Dyn.* 194, 209-221 (1992).

The invention claimed is:

1. A method of treating a subject believed to be suffering from amyotrophic lateral sclerosis, the method comprising:
   administering an inhibitor of EphA4signaling to the subject in an amount sufficient to inhibit EphA4 signaling.

2. A method of treating a subject suffering from a motor neuron disease, wherein the motor neuron disease is amyotrophic lateral sclerosis, the method comprising:
   administering to the subject an inhibitor of EphA4 signaling,
   so as to treat the motor neuron disease, wherein at least one symptom or parameter of the motor neuron disease is improved.

3. The method according to claim 2, wherein the inhibitor of EphA4 signaling is an inhibitor of EphA4 or ephrin-B2.

4. The method according to claim 2, wherein the inhibitor is selected from the group consisting of a 2,5-dimethylpyrrolyl benzoic acid derivative, a peptide having SEQ ID NO:1, a peptide having SEQ ID NO:2, a peptide having SEQ ID NO:3, ephrin-A5-Fc, and EphA4-Fc.

5. The method according to claim 2, wherein the improved parameter is prolonged survival.

6. A method of treating a subject diagnosed as suffering from amyotrophic lateral sclerosis, the method comprising:
   administering to the subject an inhibitor of EphA4 signaling, wherein the inhibitor is selected from the group consisting of a 2,5-dimethylpyrrolyl benzoic acid derivative, a peptide having SEQ ID NO:1, a peptide having SEQ ID NO:2, a peptide having SEQ ID NO:3, ephrin-A5-Fc, and EphA4-Fc,
   so as to prolong survival of the subject.

7. A method of treating a subject who has been diagnosed as suffering from amyotrophic lateral sclerosis; wherein the subject has an aberrant TDP-43, the method comprising:
   administering to the subject an inhibitor of EphA4 signaling, wherein the inhibitor is selected from the group consisting of a 2,5-dimethylpyrrolyl benzoic acid derivative, a peptide having SEQ ID NO:1, a peptide having SEQ ID NO:2, a peptide having SEQ ID NO:3, ephrin-A5-Fc, and EphA4-Fc,
   so as to prolong survival of the subject.

8. A method of treating a subject having amyotrophic lateral sclerosis with a SOD1 mutation; wherein the SOD1 mutation is selected from the group consisting of: A4V, G93A, and G37R, the method comprising:
   administering to the subject an inhibitor of EphA4 signaling, wherein the inhibitor is selected from the group consisting of a 2,5-dimethylpyrrolyl benzoic acid derivative, a peptide having SEQ ID NO:1, a peptide having SEQ ID NO:2, a peptide having SEQ ID NO:3, ephrin-A5-Fc, and EphA4-Fc,
   so as to prolong survival of the subject.

* * * * *